(12) United States Patent
Mazur et al.

(10) Patent No.: US 6,229,048 B1
(45) Date of Patent: May 8, 2001

(54) HELIANTHRONE DERIVATIVES AS ANTI-CANCER AGENTS

(75) Inventors: Yehuda Mazur, Tel-Aviv; Gad Lavie, Rehovot, both of (IL)

(73) Assignees: Yeda Research and Development Co. Ltd. at the Weizmann Institute of Science, Rehovot (IL); New York University, New York, NY (US)

( * ) Notice: Subject to any disclaimer, the term of this patent is extended or adjusted under 35 U.S.C. 154(b) by 0 days.

(21) Appl. No.: 09/494,296

(22) Filed: Jan. 31, 2000

Related U.S. Application Data

(63) Continuation-in-part of application No. PCT/IL98/00346, filed on Jul. 27, 1998.

(30) Foreign Application Priority Data

Jul. 31, 1997 (IL) ....................................................... 121440

(51) Int. Cl.[7] ....................... C07C 239/00; C07C 211/00; C07C 49/00; C07C 205/00; C07C 49/115
(52) U.S. Cl. .......................... 564/300; 564/301; 564/305; 564/308; 568/303; 568/306; 568/326
(58) Field of Search .................... 568/303, 306, 568/326; 564/305, 300, 301, 308

(56) References Cited

U.S. PATENT DOCUMENTS

| | | |
|---|---|---|
| 5,047,435 | 9/1991 | Lavie et al. . |
| 5,120,412 | 6/1992 | Mazur et al. . |
| 5,466,468 | 11/1995 | Schneider et al. . |
| 5,514,714 | 5/1996 | Meruelo et al. . |
| 5,670,491 | 9/1997 | Capraro et al. . |
| 5,686,439 | 11/1997 | Capraro et al. . |
| 5,773,460 | 6/1998 | Gaboury et al. . |

FOREIGN PATENT DOCUMENTS

| | | |
|---|---|---|
| 0 390 181 | 10/1990 | (EP) . |
| WO 90/10438 | 9/1990 | (WO) . |
| WO 93/15607 | 8/1993 | (WO) . |
| WO 94/14956 | 7/1994 | (WO) . |
| WO 94/27952 | 12/1994 | (WO) . |
| WO 96/07731 | 3/1996 | (WO) . |

OTHER PUBLICATIONS

Rodewaldet et al, "Synthesis of hypericin and related meso–nuphthodianthrones by alkaline dimerization of hydroxyanthraquinones", *Angew Chem Int Ed Engl* 89(1):46–47 (1977).
Weiner et al, "EPR Studies of Hypericin. Photogeneration of Free Radicals and Superoxide", *J Chem Soc Perkin Trans* 2:1439–1442 (1992).

Primary Examiner—Jose' G. Dees
Assistant Examiner—Alton Pryor
(74) Attorney, Agent, or Firm—Browdy and Neimark

(57) ABSTRACT

A method for treating cancer comprising administering a 1,3,4,6-tetrahydroxy-helianthrone derivative. The compounds can be used in the absence of light irradiation or for photodynamic therapy of solid tumors wherein the tumor site is subjected to light irradiation after administration of the active ingredient. A preferred compound is 10,13-dimethyl-1,3,4,6-tetrahydroxy-helianthrone.

20 Claims, 12 Drawing Sheets

HELIANTHRONE DERIVATIVES AS ANTI-CANCER AGENTS

CROSS-REFERENCE TO RELATED APPLICATION

The present application is a continuation-in-part of International Application PCT/IL98/00346, designating the United States, which International Application was filed on Jul. 27, 1998, the entire contents of which are hereby incorporated herein by reference.

FIELD OF THE INVENTION

The present invention relates to the therapeutic use of helianthrones, particularly of 1,3,4,6-tetrahydroxy-helianthrone and derivatives thereof as anti-cancer agents both in the presence and in the absence of light irradiation. In conjunction with light irradiation, these compounds are photosensitizers useful in photodynamic therapy (PDT). The present invention also provides some novel 1,3,4,6-tetrahydroxy-helianthrone derivatives.

BACKGROUND OF THE INVENTION

The discovery of the signal transduction pathways that activate cell proliferation in response to interactions between growth factors and corresponding cellular receptors, triggered an extensive search for inhibitors that can interfere with this cascade in malignancies where malignant cells undergo uncontrolled proliferation. The chemical signals in this cascade have been identified as phosphorylation of proteins either on tyrosine residues, catalyzed by a group of enzymes collectively termed protein tyrosine kinases (PTK), or on serine/threonine residues by protein kinases A, B, and C. Protein kinase C (PKC) is also an important cellular signal transducer that contains a catalytic domain which phosphorylates substrates and a regulatory domain which controls its activity. Polyhydroxylated flavones such as genistein and quercetin were identified as inhibitors of the phosphorylation kinases (Losiewicz et al, 1994).

Perylene quinones are a unique group of kinase inhibitors (Diwu et al, 1994). The first of these compounds to be thoroughly evaluated was hypericin, a potent photodynamic agent initially discovered by the present inventors to be virucidal to retroviruses (Lavie et al, 1989; Meruelo et al, 1988), and subsequently to all lipid-enveloped viruses (Tang et al, 1990). Additional studies identified hypericin as a potent and irreversible light-dependent inhibitor of protein kinase C (PKC), particularly when PKC is translocated to the cell membrane following cell activation, this PKC inhibitory activity of hypericin being possibly related to its antiretroviral activity (Takahashi et al, 1989).

Hypericin is able to act within biological systems in the dark, possibly because of a low red/ox potential, and this appears to enable electron scavenging from physiological transfer reactions (Lavie et al, 1994). The unique combination of properties of hypericin prompted its current clinical evaluation in phase II clinical trials as an anti-tumor agent in the treatment of malignant glioma (Couldwell et al, 1994). This neoplasia relies on PKC signaling for cell proliferation. Hypericin is also a potent photosensitizer capable of generating singlet oxygen and free radicals (Hadjur et al, 1994). These properties also render it useful in photodynamic therapy (PDT) of superficial tumors accessible to light irradiation.

Unfortunately, hypericin is active in only half of the cases and, in addition, may cause severe side effects, such as prolonged post-treatment sensitivity to light, a condition medically known as hypericism. It would be desirable to provide additional photosensitizing agents and cell proliferation signal transduction inhibitors which can elicit their cytotoxic effect with greater efficiency as compared with existing agents and, potentially, with lower and less severe side effects.

SUMMARY OF THE INVENTION

The present invention is based on the surprising findings that some helianthrone derivatives are capable, at micromolar concentrations, of inhibiting transduction of signals for cell proliferation and cell progression through the cell replication cycle, indicating that they can be used as antineoplastic agents for the treatment of cancer.

The present invention thus provides a method for inhibiting transduction of cell proliferation signals comprising administering to a patient in need thereof an effective amount of a compound of the general formula (I):

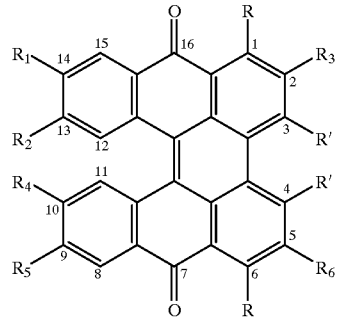

wherein R is selected from the group consisting of hydroxy, $C_1$–$C_{10}$ alkoxy, NH-$C_1$–$C_{10}$ alkyl, and NH-hydroxy($C_1$–$C_{10}$) alkyl; R' is selected from the group consisting of hydroxy and $C_1$–$C_{10}$ alkoxy; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_{1-C10}$ alkoxy, and $C_1$–$C_{10}$ alkoxycarbonyl.

In one embodiment, the treatment with the compound of formula (I) is carried out in the absence of light irradiation.

In another embodiment, the treatment of solid tumors, particularly superficial solid tumors accessible to light irradiation, with the compound of formula (I), is followed by light irradiation. Thus, in accordance with this embodiment of the invention, there is provided a method of photodynamic therapy (PDT) of tumors consisting of injecting to a patient an appropriate amount of a compound of formula (I) above, followed by local irradiation.

The present invention further provides pharmaceutical compositions comprising a compound of formula (I) and a pharmaceutically acceptable carrier.

The present invention still further provides novel compound of formula (I), excepting the compound wherein R and R' are hydroxy and $R_1$ to $R_6$ are each hydrogen.

The compound of formula (I) wherein R and R' are hydroxy and $R_1$ to $R_6$ are each hydrogen, namely 1,3,4,6-tetrahydroxy-helianthrone, was synthesized by Rodewald et al (1977) using 1,3-dihydroxy-anthrone as the starting material. The structure assigned to the resulting compound by the authors of said publication was mistaken, and found by the present inventors to be 1,3,4,6-tetrahydroxy-helianthrone.

BRIEF DESCRIPTION OF THE DRAWINGS

Figure 1A:
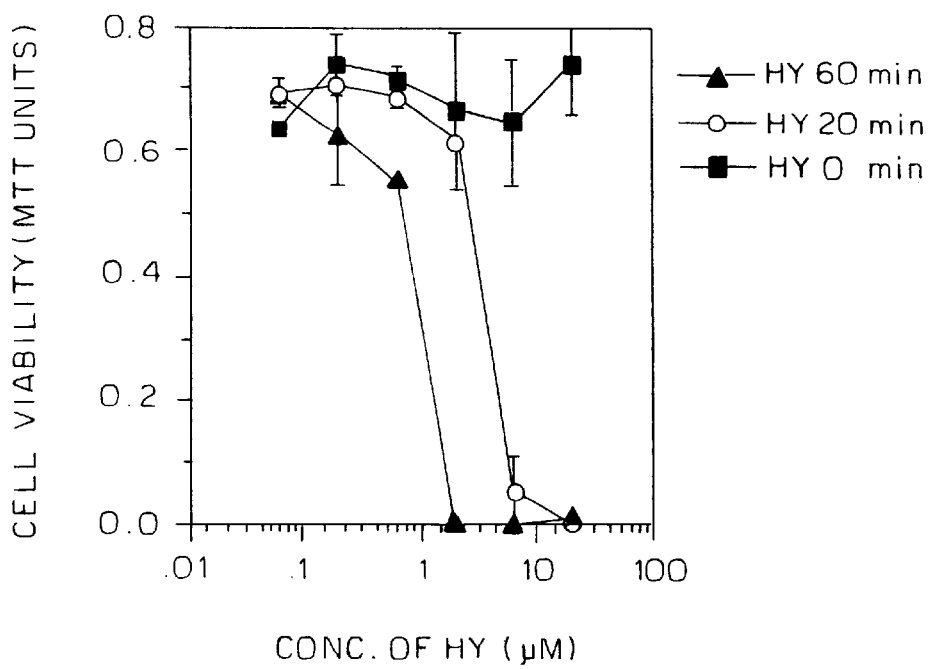
Figure 1B:
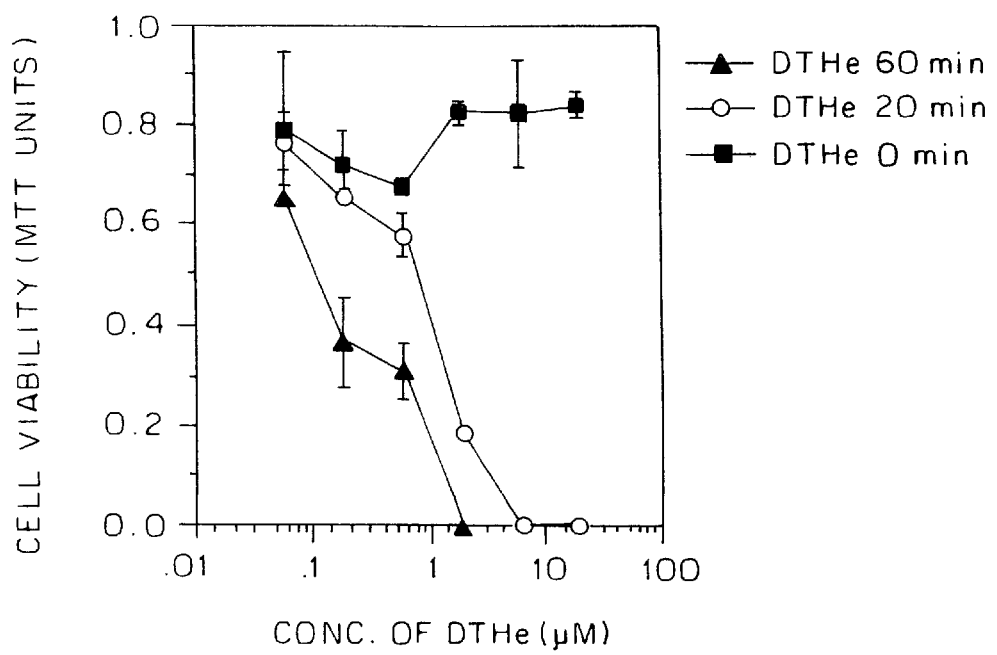

FIGS. 1A–B show the photodynamic effects of various concentrations of hypericin (HY, FIG. 1A) and 10,13- dimethyl-1,3,4,6-tetrahydroxy-helianthrone (DTHe, FIG. 1B) on leukemic HL-60 cell viability as monitored by the MTT assay, using two different doses of light irradiation.

Figure 2A:
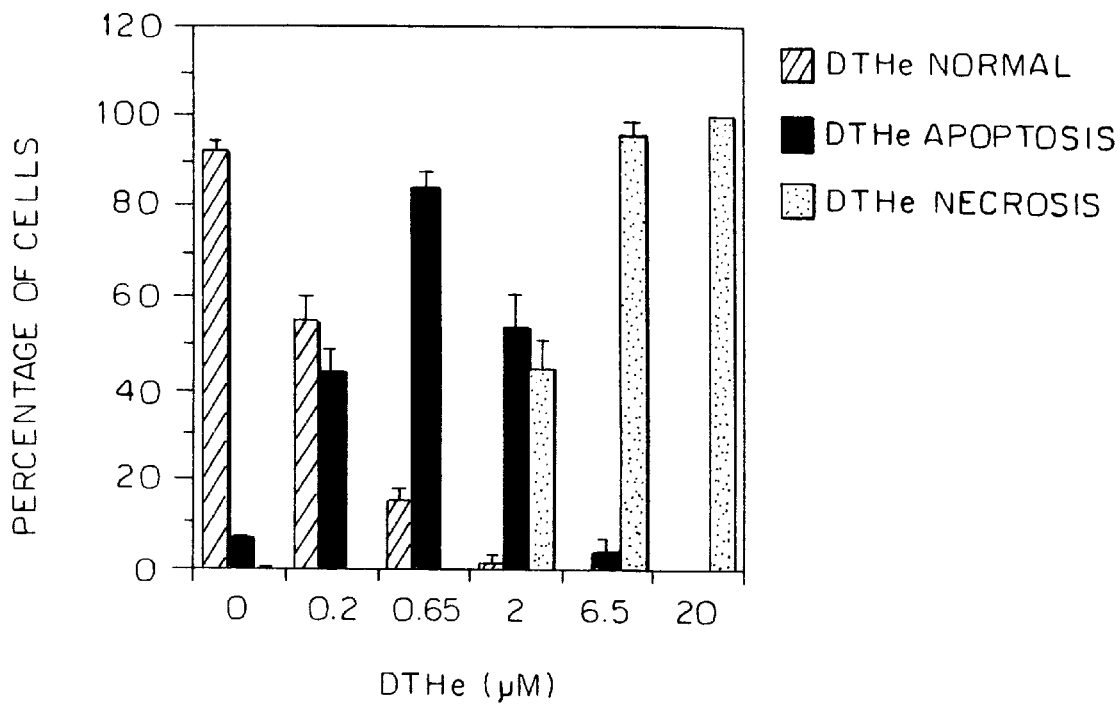
Figure 2B:
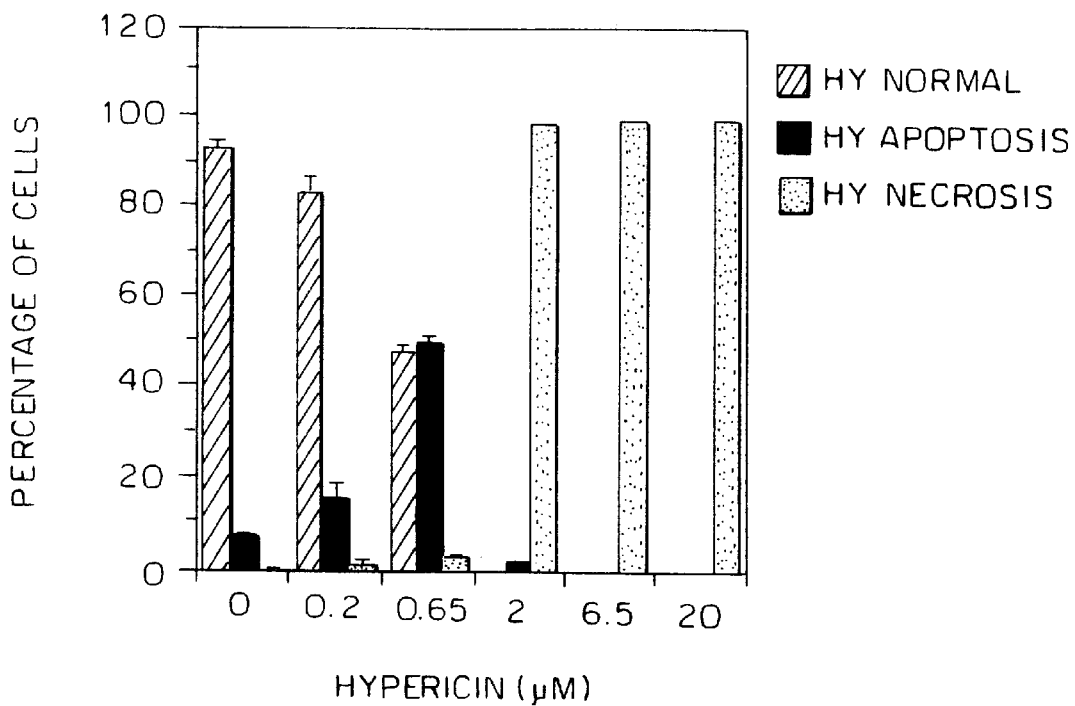

FIGS. 2A–B show microscopic analysis of the mechanisms of cell death (apoptosis, necrosis) induced by the photodynamic effects of various concentrations of DTHe (FIG. 2A) and hypericin (HY, FIG. 2B) on HL-60 cells.

Figure 3A:
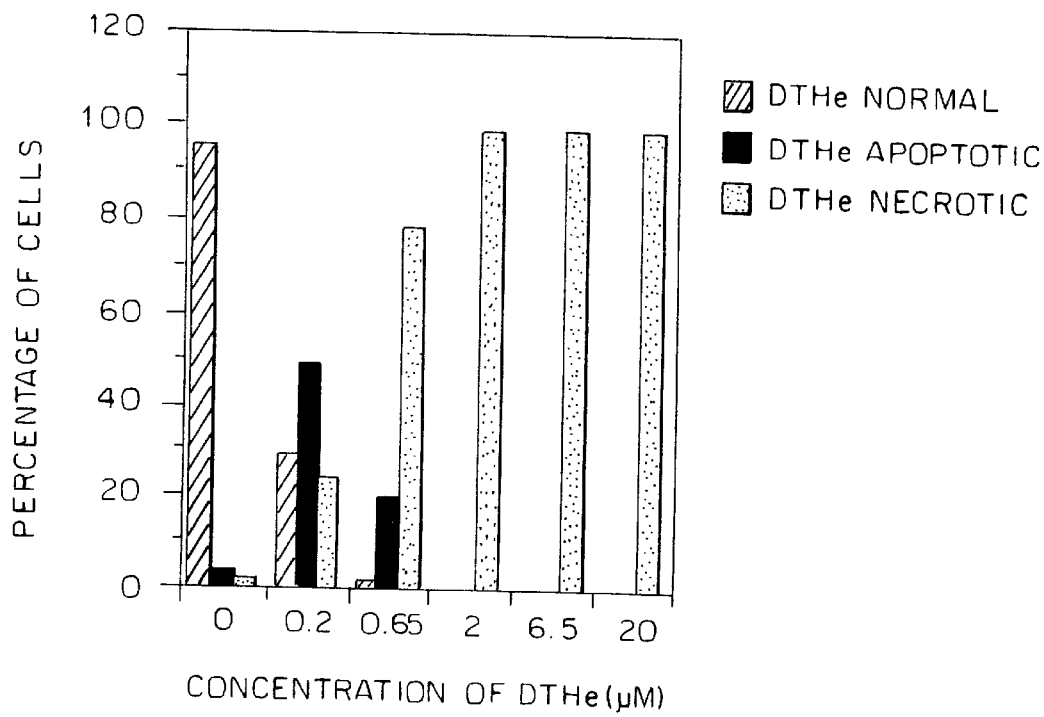
Figure 3B:
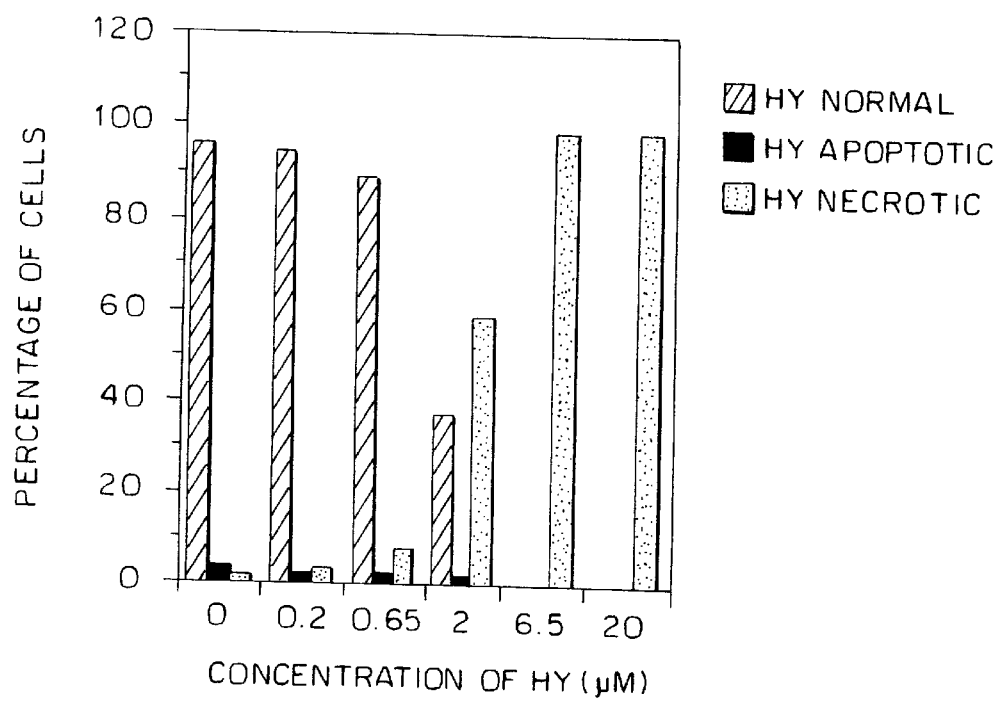

FIGS. 3A–B show microscopic analysis of the mechanisms of cell death (apoptosis, necrosis) induced by the photodynamic effects of various concentrations of DTHe (FIG. 3A) and hypericin (HY, FIG. 3B) on K-562 cells.

Figure 4:
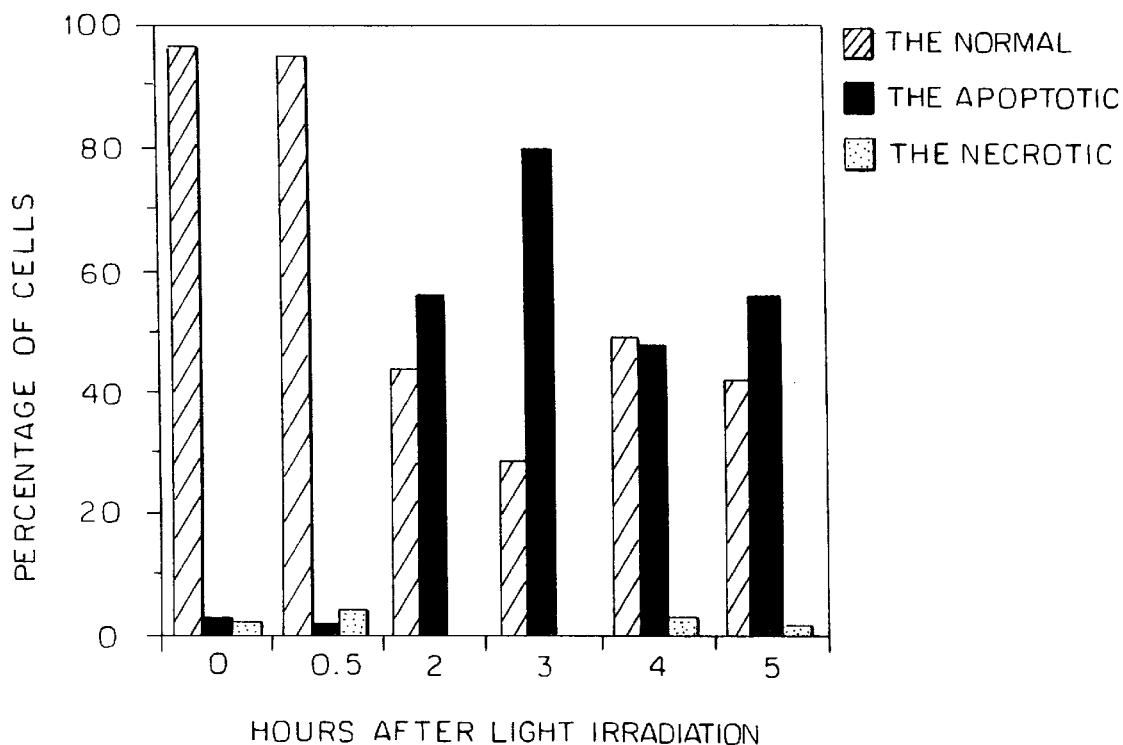

FIG. 4 shows the percentage of HL-60 cells featuring normal, apoptotic or necrotic morphology at different periods of time after administration of 0.65 $\mu$M 1,3,4,6-tetrahydroxy-helianthrone (THe) and light irradiation.

Figure 5:
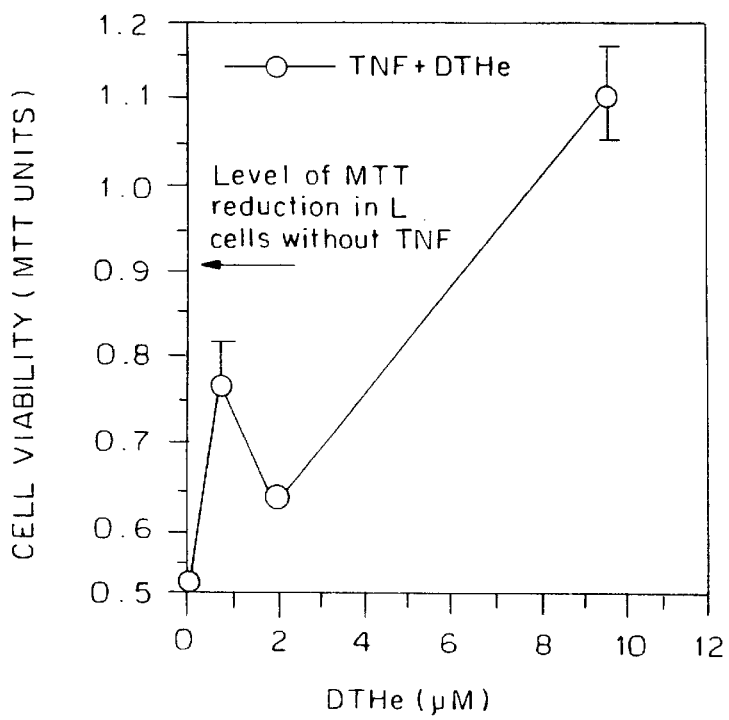

FIG. 5 shows protection of murine L cells by DTHe from TNF-$\alpha$ induced apoptosis.

Figure 6A:
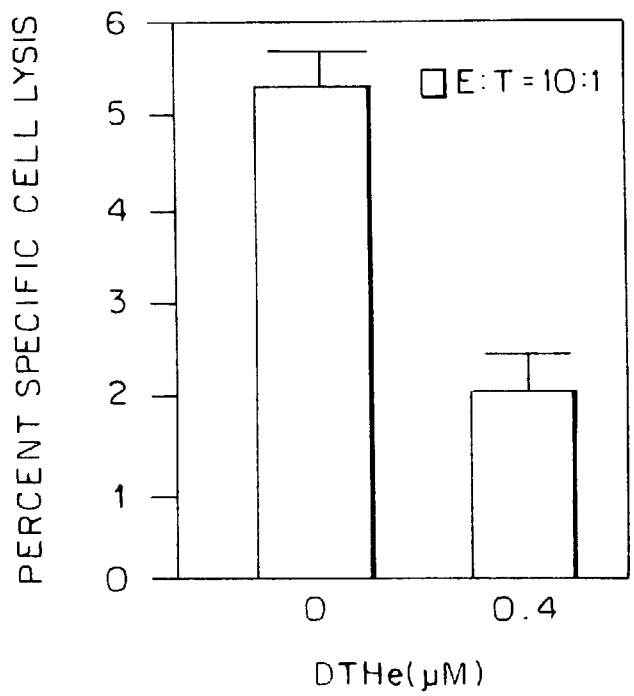
Figure 6B:
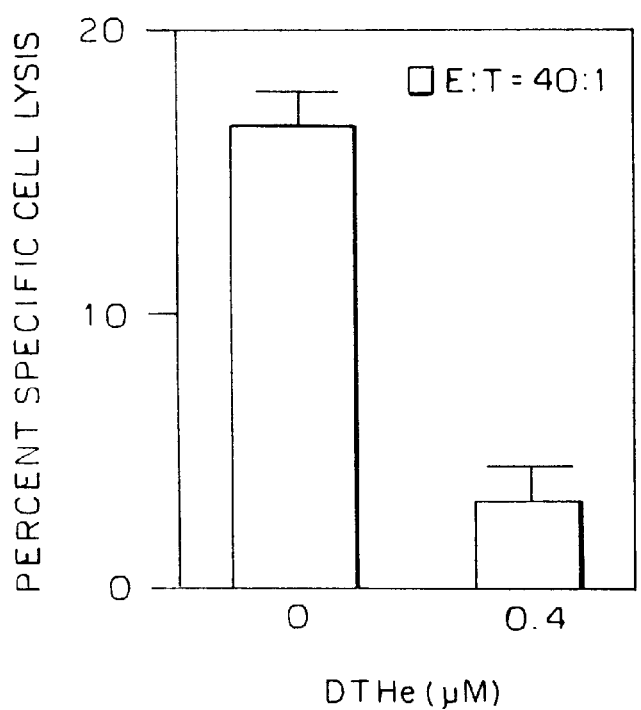

FIGS. 6A–B show effect of DTHe on natural killer (NK) cell cytotoxic activity against K-562 target cells by bringing into contact effector (E) NK-cells and K-562 target (T) cells at ratios R:T=10:1 (FIG. 6A) and E:T=40:1 (FIG. 6B).

Figure 7:
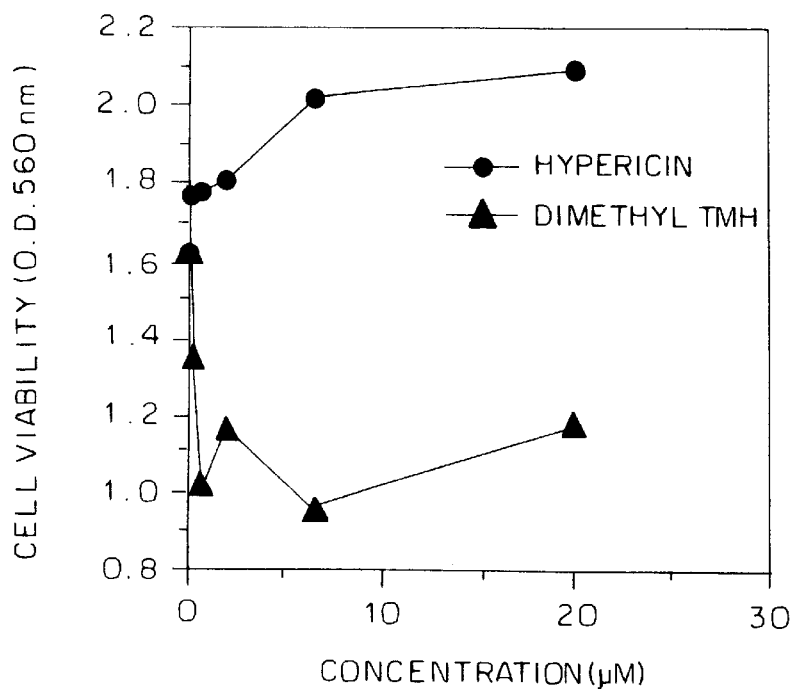

FIG. 7 shows the effects of various concentrations of 10,13-dimethyl-1,3,4,6-tetramethoxy-helianthrone (dimethyl-TMH) and hypericin on U251 human glioblastoma cell viability in complete darkness.

Figure 8:
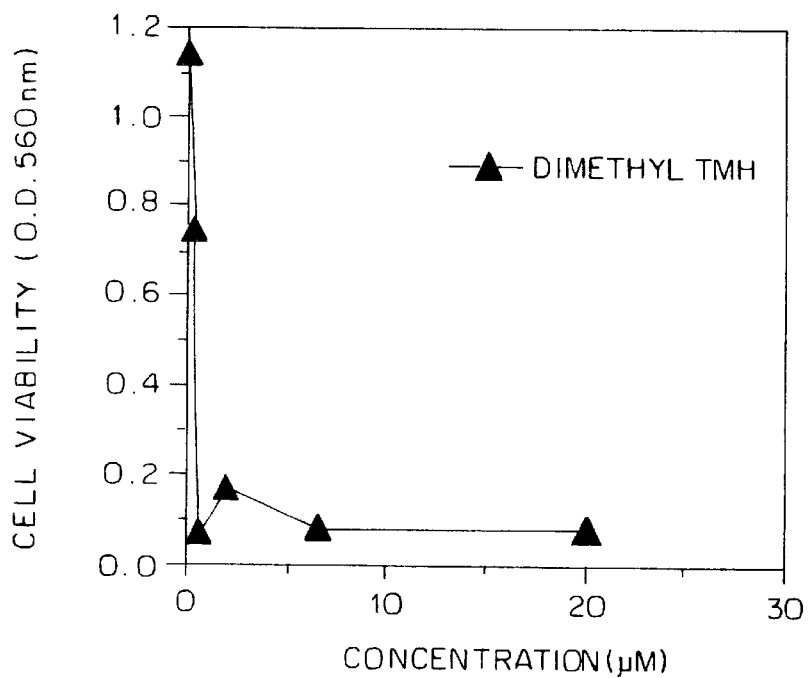

FIG. 8 shows the effects of various concentrations of dimethyl-TMH on LAN5 neuroblastoma cell viability in complete darkness.

Figure 9:
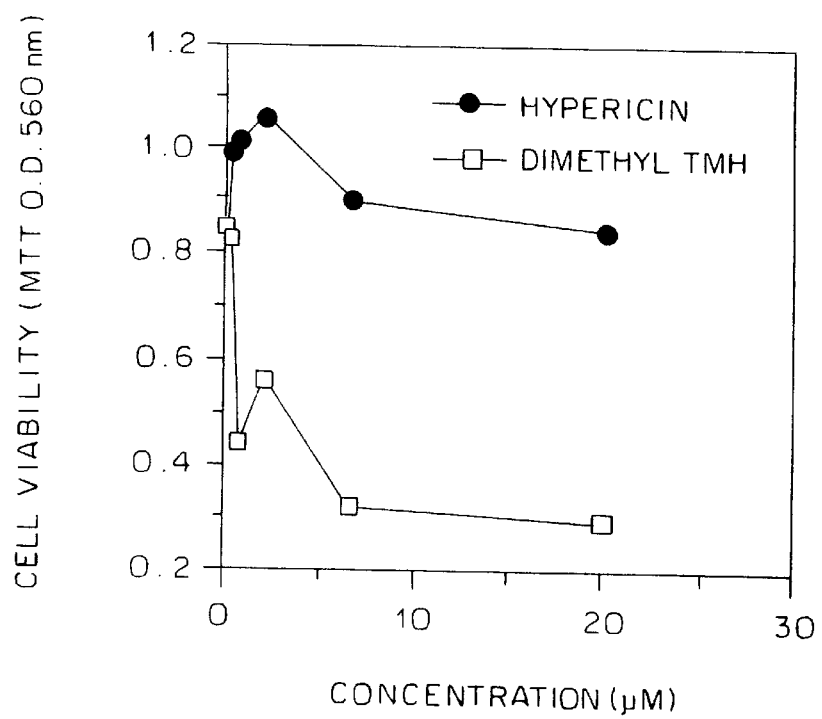

FIG. 9 shows the effects of various concentrations of dimethyl-TMH and hypericin on U87MG glioblastoma cell viability in complete darkness.

Figure 10:
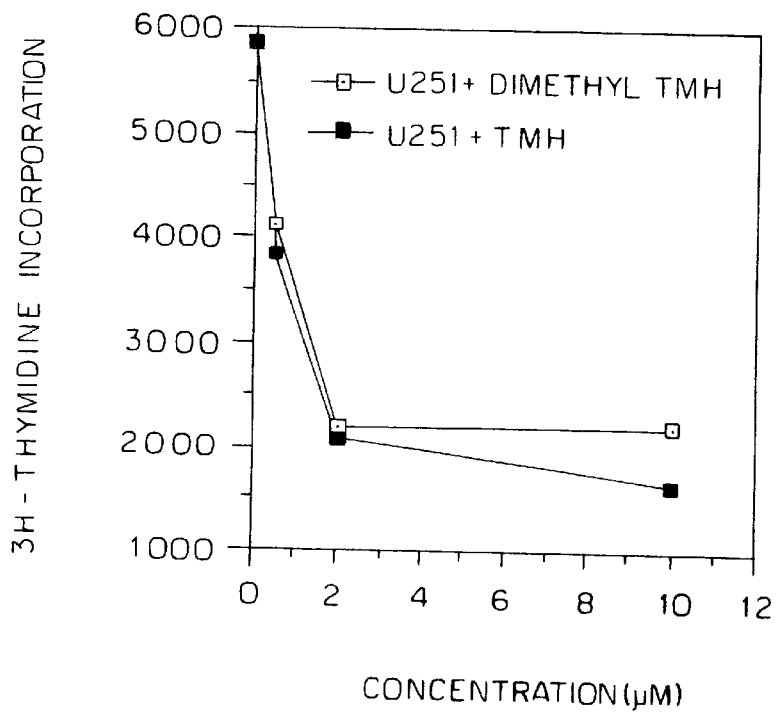

FIG. 10 shows the effects of various concentrations of dimethyl-TMH and TMH on U87MG glioblastoma cell viability in complete darkness for 48 hours.

Figure 11:
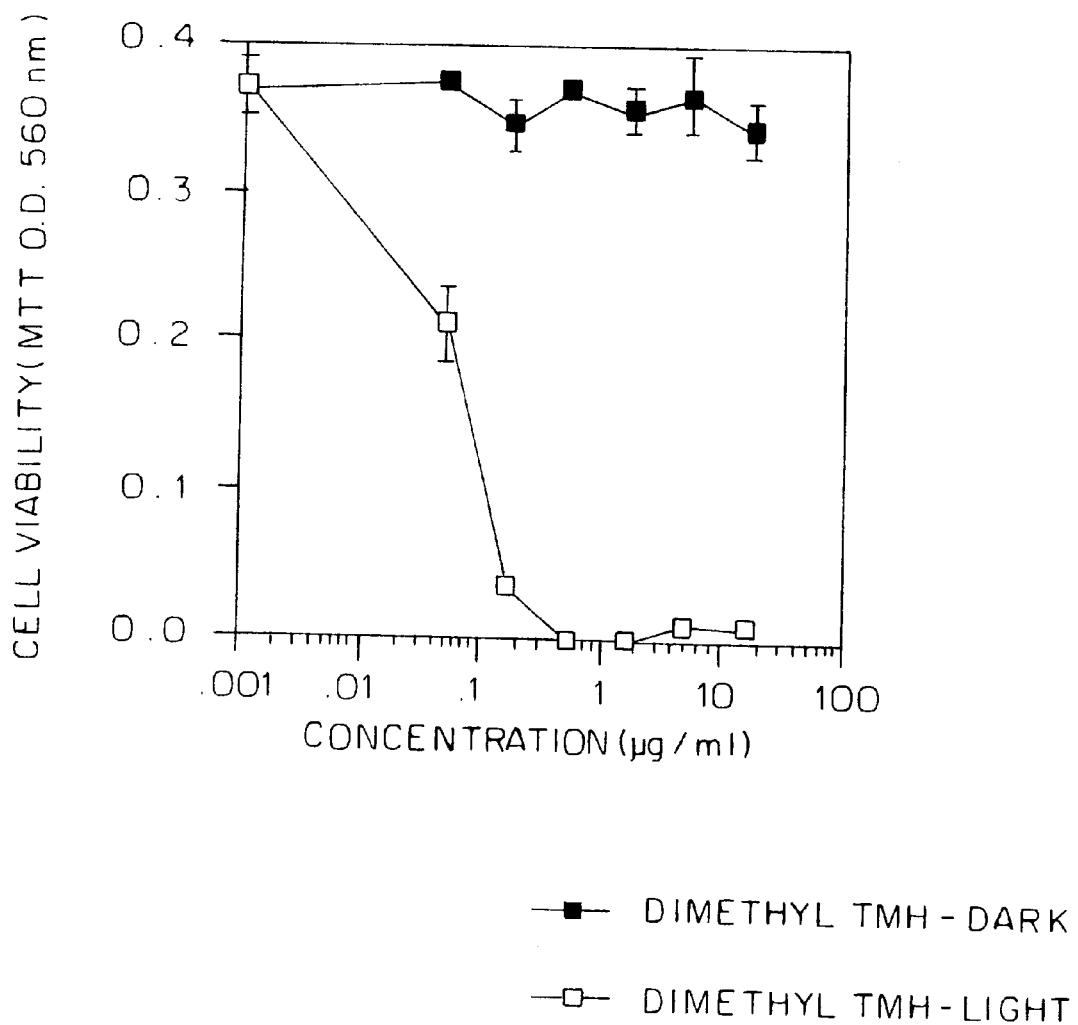

FIG. 11 shows the light-dependent photodynamic effects of dimethyl-TMH on primary post-mitotic human peripheral blood lymphocytes (PBL) viability in the dark and in conjunction with light.

Figure 12A:
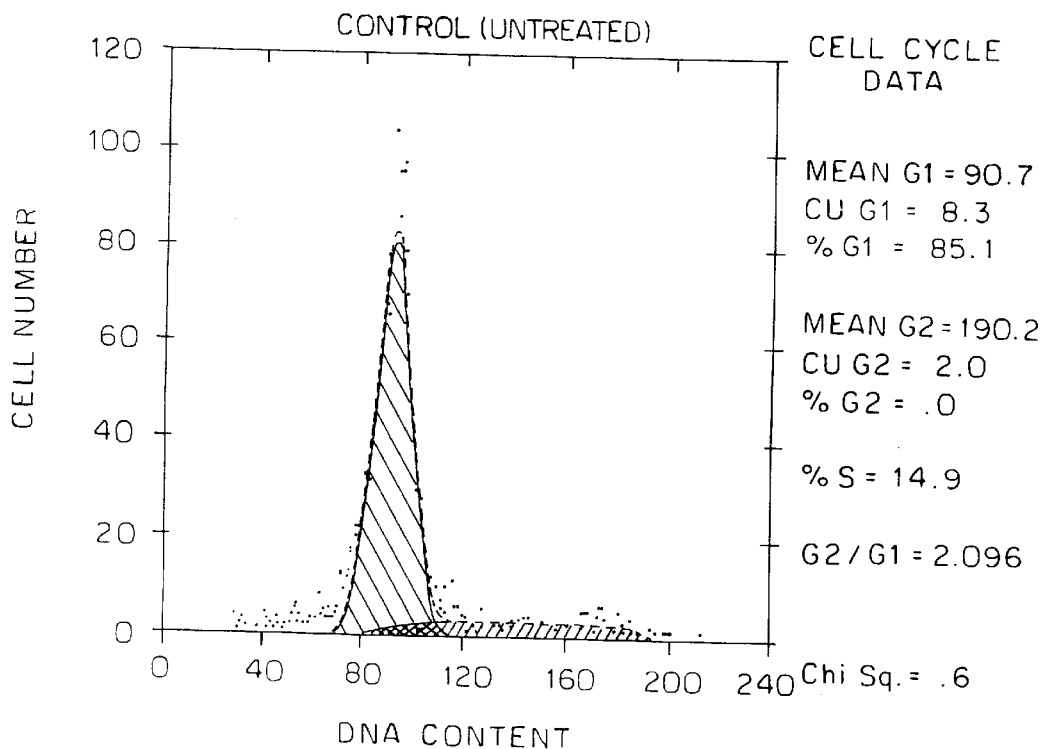
Figure 12B:
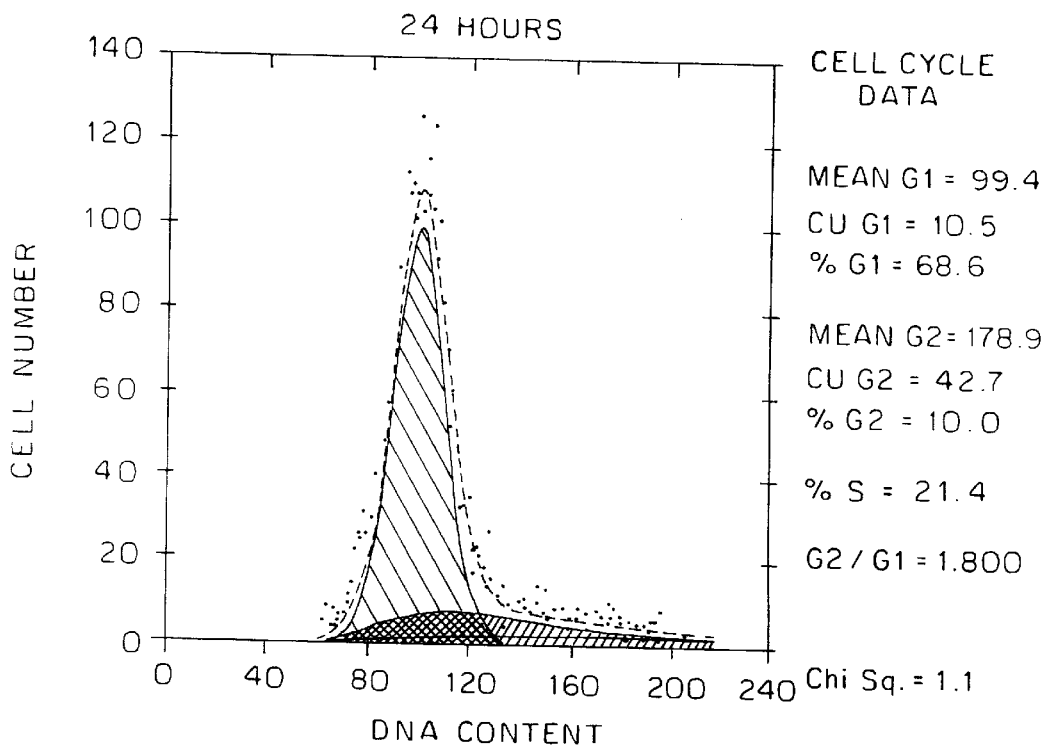
Figure 12C:
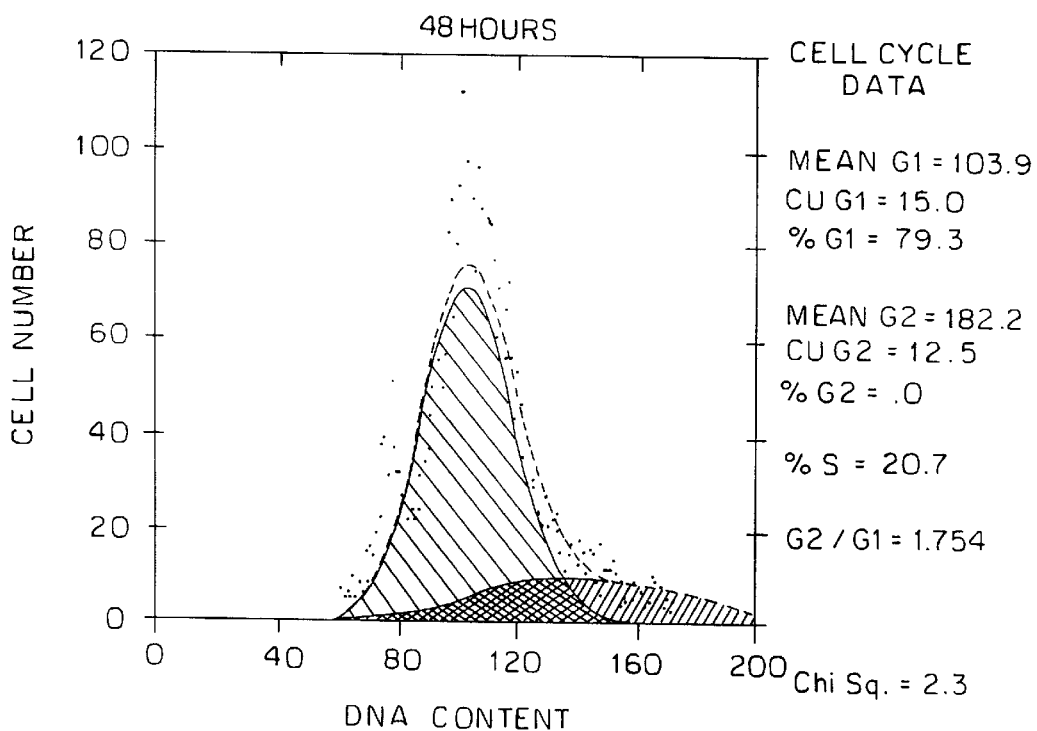
Figure 12D:
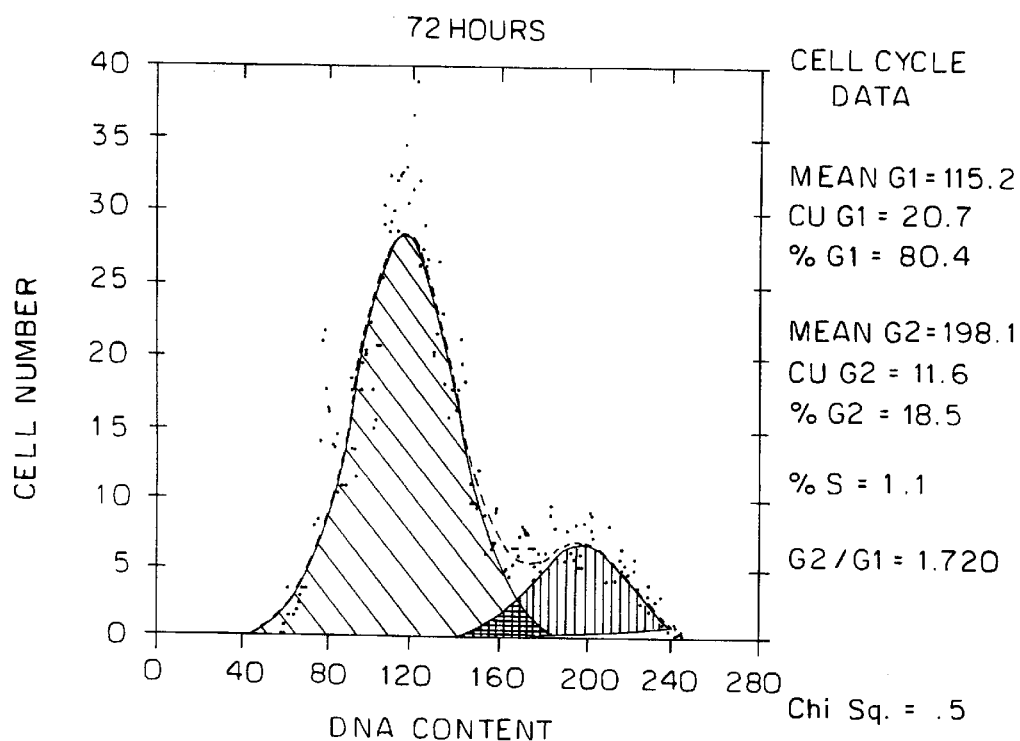

FIGS. 12A–D show the effects of 10 $\mu$M dimethyl-TMH on U251 human glioblastoma cells in culture without (FIG. 12A) and after treatment for 24 hours (FIG. 12B), 48 hours (FIG. 12C), and 72 hours (FIG. 12D).

Figure 13A:
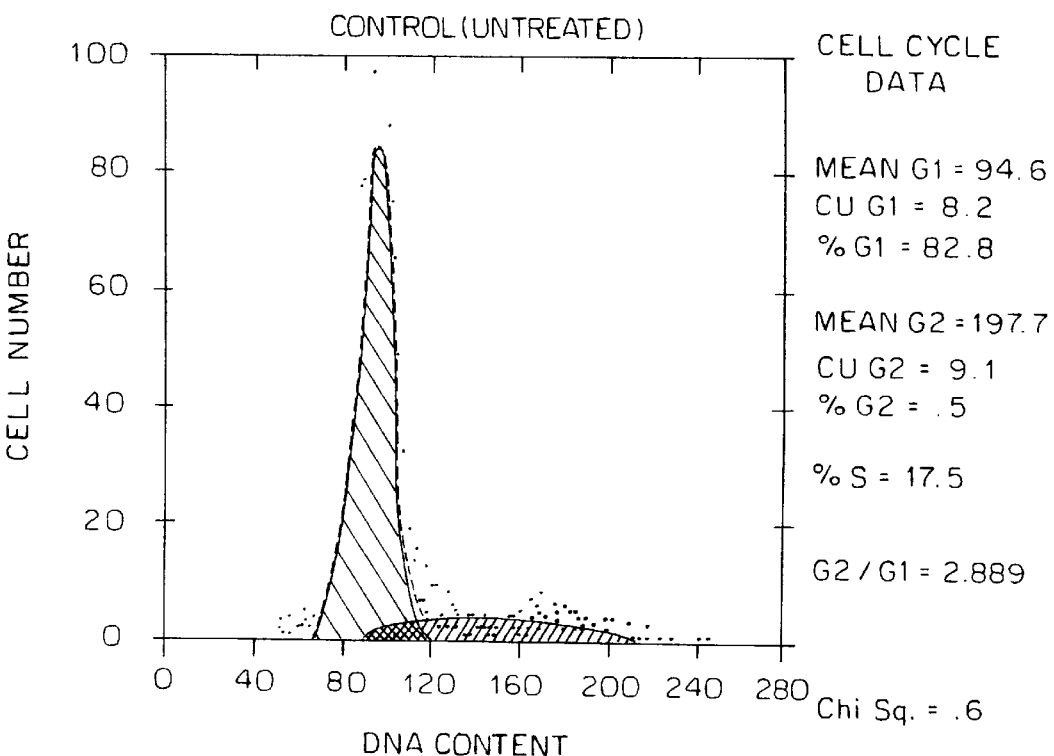
Figure 13B:
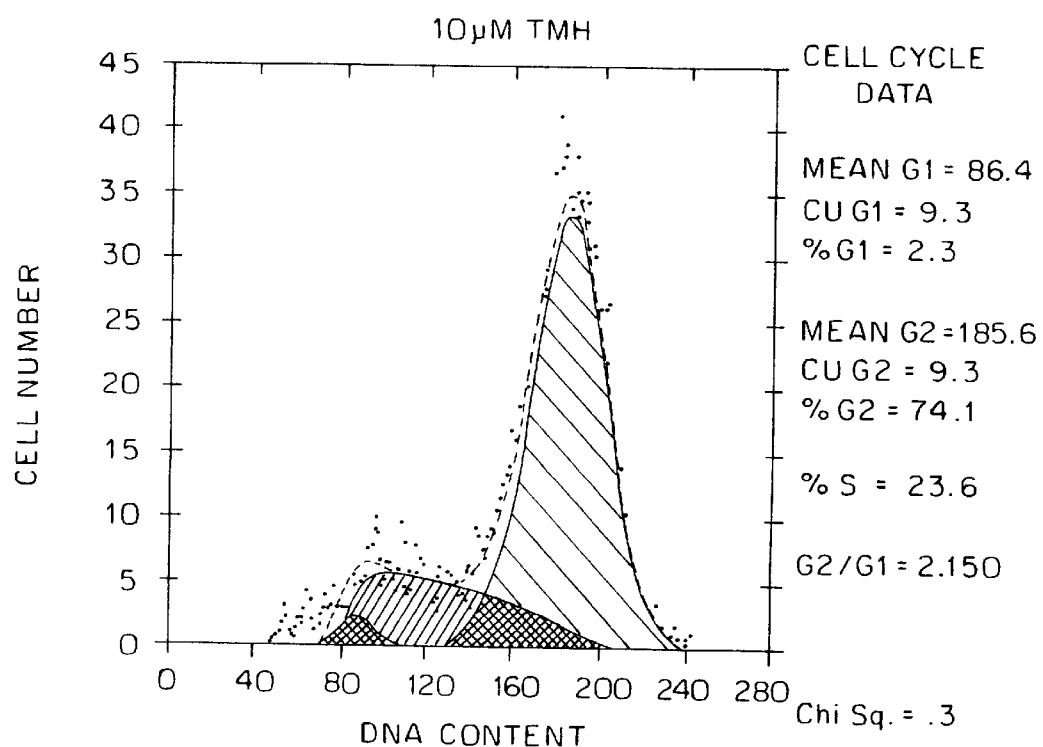
Figure 13C:
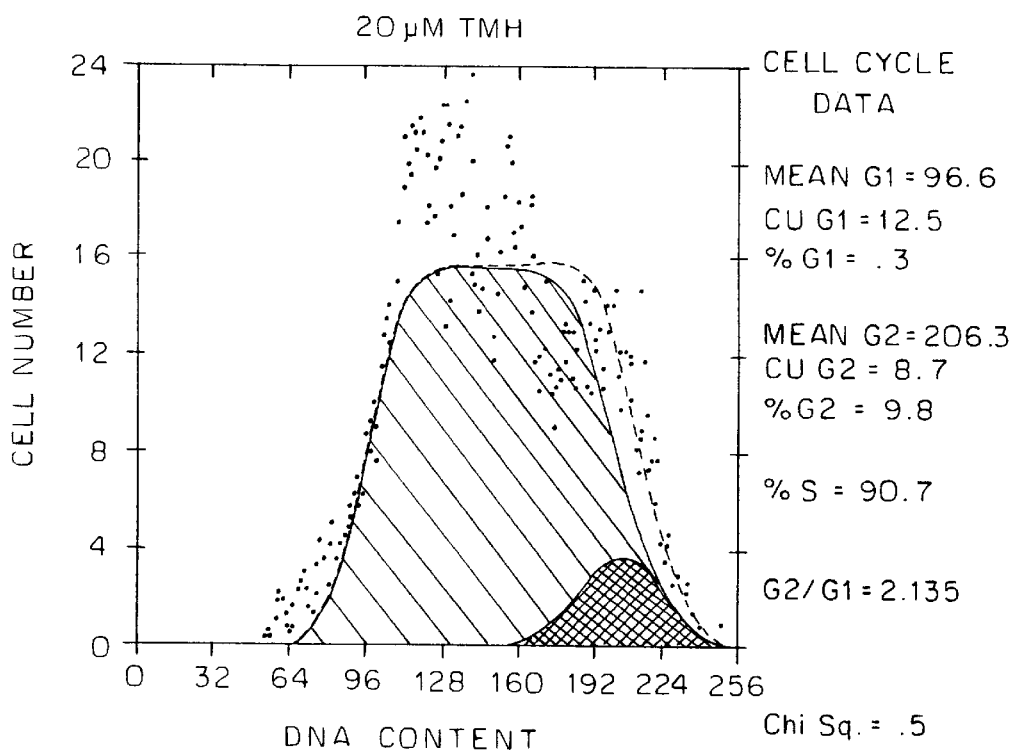

FIGS. 13A–C show the dose response effects of 10 pM (FIG. 13B) and 20 $\mu$M (FIG. 13C) dimethyl-TMH on U251 human glioblastoma cells in culture. Control (untreated, FIG. 13A).

Figure 14:
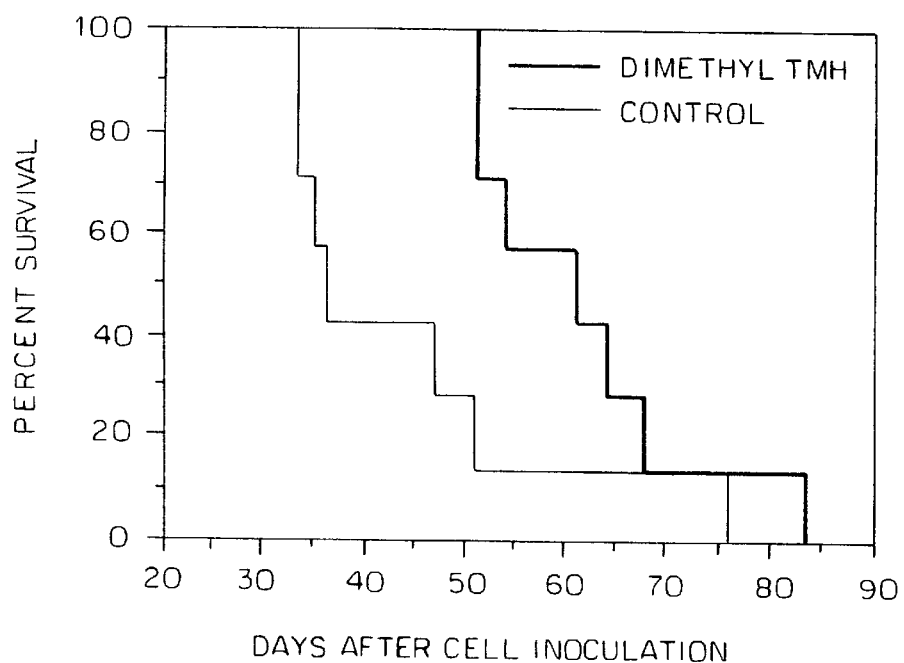

FIG. 14 shows percent survival of BALB/c mice inoculated with squamous cell carcinoma cells after treatment with dimethyl-TMH.

DETAILED DESCRIPTION OF THE INVENTION

In the compounds of formula (I), R is selected from the group consisting of hydroxy, $C_1$–$C_{10}$ alkoxy, NH-$C_1$–$C_{10}$ alkyl, and NH-hydroxy($C_1$–$C_{10}$)alkyl; R' is selected from the group consisting of hydroxy and $C_1$–$C_{10}$ alkoxy; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl. In a preferred embodiment, $R_1$=$R_5$, $R_2$=$R_4$ and/or $R_3$=$R_6$.

As used herein, "$C_1$–$C_{10}$ alkyl", "$C_1$–$C_{10}$ alkoxy" and "$C_1$–$C_{10}$ alkoxycarbonyl" refer to straight or branched radicals having 1 to 10 carbon atoms. Examples of such alkyl radicals are, without being limited to, methyl, ethyl, propyl, isopropyl, butyl, hexyl, and octyl. Examples of such alkoxy radicals are, without being limited to, methoxy, ethoxy, propyloxy, isopropyloxy, butoxy, hexyloxy, and octyloxy. Examples of such alkoxycarbonyl radicals are, without being limited to, methoxycarbonyl, ethoxycarbonyl, propyloxycarbonyl. In one preferred embodiment, R, R' and $R_1$ to $R_6$ are methyl, but longer aliphatic chains envisaged in these positions instead of the methyl group may have advantages such as prolongation of biological activity due to better retention by cells and requiring less frequent administration.

Preferred compounds are those wherein the two Rs at positions 1 and 6 are hydroxy, methoxy, butylamino or hydroxyethylamino, the two R's at positions 3 and 4 are hydroxy or methoxycarbonyl, $R_2$ and $R_5$ at positions 14 and 9 are hydrogen, and $R_3$ and $R_6$ at positions 2 and 5 are hydrogen or bromo. Examples of such preferred compounds are 1,3,4,6-tetrahydroxy-helianthrone, 1,3,4,6-tetramethoxy-helianthrone, 10,13-dimethyl-1,3,4,6-tetrahydroxy-helianthrone, 10,13-di(methoxycarbonyl)-1,3,4,6-tetramethoxy-helianthrone, 1,6-di-N-butylamino-3,4-dimethoxy-helianthrone, 1,6-di-N-butylamino-3,4-dimethoxy-10,13-dimethyl-helianthrone, 1,6-di-(N-hydroxyethylamino)-3,4-dimethoxy-helianthrone, 2,5-dibromo-1,3,4,6-tetrahydroxy-helianthrone, 2,5-dibromo-10,13-dimethyl-1,3,4,6-tetrahydroxy-helianthrone, and, most preferably, 10,13-dimethyl-1,3,4,6-tetramethoxy-helianthrone.

The compounds of the formula (I) according to the invention in which $R_2$ and $R_4$ are each lower alkyl can be prepared by the method described in U.S. Pat. No. 5,120,412 using as a starting material a 1,3-dihydroxy-6-(lower alkyl)-anthraquinone of the formula (II):

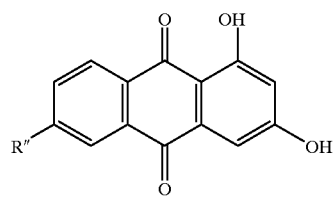

II in which R" is lower alkyl. Compound II is reduced to the corresponding anthrone of the formula (III)

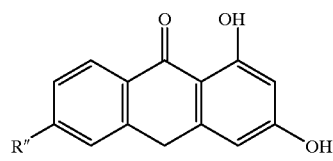

III in which R" is as defined above and compound III is condensed to obtain desired compounds of formula (I) in which R is lower alkoxy.

Other compounds of formula (I) can be prepared in an analogous manner using appropriately substituted 1,3-dihydroxy-anthraquinones.

The compounds of formula (I) in which $R_2$ and $R_4$ are each lower alkoxycarbonyl can be prepared from the diacetyl derivatives of the compound of formula (II) above in which R" is methyl, by oxidation with $CrO_3$ to form the compound of the formula (IV)

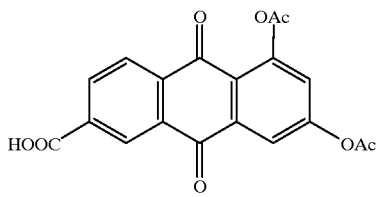

which is then dimerized by the method of Spitzner (1977) to form a compound of formula (I) in which R is carboxy which is then esterified with lower alkanol to obtain the desired product of formula (I) in which $R_2$ and $R_4$ are lower alkoxycarbonyl.

The compounds of formula (I) in which each R at positions 1 and 6 is alkylamino or hydroxy alkylamino may be obtained by amination of the corresponding compound of formula (I), in which each R is alkoxy, with an alkyl amine such as butyl amine, or a hydroxyalkyl amine such as ethanolamine. These amino derivatives have the advantage of exhibiting a light absorption maximum in the long visible range, wavelengths>620 nm, which offers deeper penetration of light into tissues at greater depths during photodynamic therapy without quenching or competing for tissue porphyrins.

According to the present invention, compounds are provided which inhibit cell proliferation through the mitotic cycle. It was surprising to discover that these compounds, and particularly, 10,13-dimethyl-1,3,4,6-tetramethoxy-helianthrone (herein designated "dimethyl-TMH"), are highly potent in deregulating several cell-cycle related checkpoints, which coordinate the orderly passage of cells through the different phases of the mitotic cycle. In this cycle, cells in G0 resting phase move into G1 protein and RNA accumulation phase. The cells then enter the S phase in which the genomic DNA is duplicated. As DNA duplication is completed, the cells are in the G2 phase with double the amount of DNA, ready for division, and progress into cell division M phase (mitosis), in which the cell divides into two daughter cells. Dimethyl-TMH was found to possess basic inhibitor activity of transduction of cell proliferation signals and to arrest malignant cells, including glioblastoma and neuroblastoma cells at mid S and G2 phases of the cell replication cycle. In mice bearing squamous cell carcinoma tumors, dimethyl-TMH completely inhibited the spread of the tumor into multiple foci and the tumors hardened, became necrotic, and fell off after prolonged treatment.

In human malignant glioblastoma cell lines, the blockage of orderly advance of the cells through the different cycle phases culminated in cell death (FIG. 7), with dimethyl-TMH identified to be more potent than hypericin in killing the tumor cells in culture in complete darkness. Cell killing by dimethyl-TMH occurred at doses in which hypericin had no effect on the cultures. Surprisingly, dimethyl-TMH was equally more potent than hypericin in the photodynamic induction of cell death when treatments were performed in conjunction with light. The mechanisms that operate in the dark were very different from those that mediate light-induced photosensitization. In the dark, cell death occurs approximately four days after the compound is administered, whereas the cells died within 2–3 hours with light.

On normal human peripheral blood mononuclear cells, dimethyl-TMH had no effect on cell viability. Furthermore, intraperitoneal administration of the compound to BALB/c mice on a daily basis for one week had no adverse effect on the animals. In BALB/c mice bearing anaplastic squamous cell carcinoma tumors, treatments with 200 μg/mouse every other day resulted in significant inhibition of tumor growth compared to tumor bearing untreated control mice.

The pharmaceutical compositions of the invention will be administered to the patient by standard procedures. The amount of compound to be administered and the route of administration will be determined according to the kind of tumor, stage of the disease, age and health conditions of the patient. In the PDT embodiment, the amount will be much lower than the currently used dosage of Photofrin II of about 20–40 mg/kg body weight. The preferable routes of administration are intravenous or direct injection into the solid tumor of the aqueous solution of the active compound comprising conventional pharmaceutically acceptable carriers and additives, and topical treatment of the skin tumors with suitable topical compositions. In disseminated tumors with metastases or systemic cancers such as leukemias and lymphomas, the preferential routes are systemic routes, the intravenous or the oral routes being preferred.

The compounds of the present invention can be administered to the patient either in the absence of light irradiation or as part of a photodynamic therapy regimen. The method of photodynamic therapy of cancer according to the invention, comprises administering to a patient afflicted with a solid tumor cancer, a pharmaceutical composition comprising a compound of formula (I) according to the invention, and then irradiating the tumor site with strong light sources at 450–600 nm, preferably at 460–490 nm.

The compounds of the present invention can be used to treat various types of cancers, including, but without being limited to, squamous cell carcinoma, basal cell carcinoma, melanoma, Kaposi sarcoma, breast carcinoma, hemangioma, meningioma, astrocytoma, neuroblastoma, carcinoma of the pancreas, colorectal carcinoma, colon carcinoma, transitional cell carcinoma of the bladder, and carcinoma of the larynx, chronic myeloid leukemia, acute lymphocytic leukemia, acute promyelocytic leukemia, multiple myeloma, T-cell lymphoma and B-cell lymphomas. In the PDT therapy, they can further be used to treat benign tumors such as verruca vulgaris, condyloma and fibroma.

The invention will now be illustrated by the following non-limiting Examples.

EXAMPLES

For convenience and better understanding, the section of the Examples is divided into two subsections: (I) Chemical Section, describing the synthesis of the helianthrone compounds, and (II) Biological Section, describing the biological effects of the helianthrone compounds in vitro and in vivo.

(I) CHEMICAL SECTION

Example 1: Preparation of 10,13-dimethyl-1,3,4,6-tetrahydroxy-helianthrone (dimethyl THe)

1,3-dihydroxy-6-methyl-anthraquinone (II, R"=$CH_3$) (380 mg) was dissolved in 45 ml glacial acetic acid, heated to boiling and then treated dropwise with a solution of $SnCl_2 \cdot 2H_2O$ (9.6 g) in concentrated HCl (24 ml) under stirring at 90° C. for two hours. The reaction mixture was then refluxed for an additional hour. The acetic acid was removed under reduced pressure and the residue treated with 200 ml of water. The formed precipitate was filtered and dried to give 300 mg of the anthrone (III, R"=$CH_3$) which, without purification, was dissolved in a mixture of 9.45 ml of pyridine and 0.94 ml of piperidine. The resulting solution was treated with 940 mg of pyridine N-oxide and 0.05 g of ferrous sulphate heptahydrate and then refluxed for one hour at 100° C. The reaction mixture was concentrated under vacuum and the solid product obtained was dissolved in acetone, then filtered, and the acetone solution evaporated to dryness. The residue was chromatographed on a silica gel column. The fraction eluted with a mixture of ethyl acetate-methanol (85:15) gave a red solution which was evaporated to dryness to give 60 mg (20% yield) of the title compound 10,13-dimethyl-1,3,4,6-tetrahydroxy-helianthrone (THe).
NMR δ (CD$_3$CN): 2.13 (6H s 10,13-CH$_3$), 6.33 (2H s 2,5-H), 7.33 (2H d J=8 Hz 9,14-H), 7.66 (2H s 11,12-H), 8.29 (2H d J=8 Hz 8,15-H), 16.14 (1H s 3 or 4-H).

Example 2: Preparation of 10,13-di (methoxycarbonyl)-1,3,4,6-tetrahydroxy-helianthrone 2.1 1,3-Dihydroxy-6-methyl-anthraquinone (II, R"=CH$_3$) (100 mg) was dissolved in pyridine (0.75 ml), treated with acetic anhydride (3.8 ml) and then refluxed for three hours. The reaction mixture was cooled to 0° C. in an ice bath and the formed precipitate was filtered, washed with water and crystallized from ethyl acetate and hexane to give the 1,3-diacetoxy-6-methyl anthraquinone (80 mg).
NMR δ (CDCl$_3$): 2.34 (3H s 6-CH$_3$), 2.47 (3H s OAc), 2.50 (3H s OAc), 7.24 (1 H s 2-H), 7.56 (1 H dd J=8,0.6 Hz 7-H), 7,97 (1H d J=2.4 Hz 4-H), 8.03 (1H br 5-H), 8.09 (lH d J=8 Hz 8-H).

2.2 1, 3-Diacetoxy-6-methyl-anthraquinone (20 mg) (obtained in Example 2.1) was dissolved in a 1:1 mixture of acetic anhydride and acetic acid (16.6 ml) at 50° C. and added dropwise to a solution of CrO$_3$ (135 mg) in aqueous 40% acetic acid (2.7 ml). The reaction mixture was then stirred for three hours, cooled and poured into 200 ml of water. After being left for two hours, the solution was extracted with ethyl acetate, washed with water and then extracted twice with saturated sodium bicarbonate solution. The aqueous phase was washed twice with methylene chloride, acidified with dilute HCl and extracted with ethyl acetate. The organic extract was evaporated to dryness yielding 18 mg of 1,3-diacetoxy-6-carboxy-anthraquinone (IV). UV-vis (EtOH) λ$_{max}$353, 483, 530 sh, 564 nm (ε 22000, 30000, 20000, 15000)
NMR δ (CD$_3$OD): 6.50 (1H s 2-H), 7.17 (1H s 5-H), 8.50 (2H dd J=34, 6 Hz 7,8-H), 8.77 (1H br 1-H).

2.3 1,3-Diacetoxy-6-carboxy-anthraquinone (IV) (300 mg) (obtained in Example 2.2) was added to a mixture of potassium tert. butoxide (160 mg), hydroquinone (186 mg) and water 5.2 ml). This mixture was sonicated for 30 minutes and then introduced to an ampoule from which the air was removed with a stream of argon. The ampoule was sealed and left at 130° C. for 21 days. The ampoule was cooled, opened, and its content poured into water. The resulting material was extracted with ethyl acetate. The organic extract was evaporated to dryness and the residue was chromatographed on a silica gel column. The material eluted with ethyl acetate: methanol (1:1) consisted of 30 mg of 1,3,4,6-tetrahydroxy-10,13-dicarboxy-helianthrone (I, R=COOH).
NMR δ (CD$_3$COCD$_3$): 6,53 (2H s 2,5-H), 8.05 (2H, d J=7 Hz 8,15-H), 8.40 (2H d J=9 Hz 8,15-H), 8.49 (d J=9 Hz 11,12-H).

2.4 The diacid obtained in Example 2.3 (20 mg) was treated with absolute MeOH (10 ml) containing 3 drops of sulfuric acid and refluxed for 24 hours. The resulting solution was washed with a saturated solution of sodium bicarbonate and water. Evaporation to dryness resulted in a residue which was chromatographed on silica gel. Elution with ethyl acetate: methanol (4:1) gave 11 mg of the title compound 1,3,4,6-tetrahydroxy-10,13-di (methoxycarbonyl)-helianthrone (I, R=COOCH$_3$).
UV-vis (EtOH) λ $_{max}$371, 496, 550 sh, 580 nm (ε 27000, 32000, 25000, 26000)
NMR δ (CD$_3$COCD$_3$): 3.69 (6H s COOCH$_3$) , 6,38 (2H s 2-H, 5-H), 8.05 (2H d J=2 Hz 8,15-H), 8.47 (2H s 11,12-H), 8.59 (2H d J=2 Hz 9,14-H).

Example 3: Preparation of 1,3,4,6-tetrahydroxy-helianthrone (THe)

1,3-Dihydroxy-anthrone (1 g) was dissolved in a mixture of 25 ml pyridine and 2 ml piperidine, and treated with 2 g pyridine N-oxide and 0.1 g ferrous sulfate heptahydrate. The reaction mixture was refluxed for one hour at 100° C. The mixture was then concentrated under vacuum and the residue treated with 50 ml of 3% aqueous HCl, to give a precipitate which was filtered and washed with water. The resulting material was chromatographed over a silica gel column using as an eluent a mixture of ethyl acetate:hexane 1:1, to give 0.6 g of the title compound 1,3,4,6-tetrahydroxy-helianthrone (I, R=R'=R$_1$–R$_6$=OH).
NMR δ (CD$_3$OD): 6.50 (s); 7.49, 7.22 (each ddd, J=7.5, 1.5 Hz); 8.32, 7.72 (each dd,J, J=7.5, 1.5 Hz).

Example 4: Preparation of 1,3,4,6-tetramethoxy-helianthrone (TMH).

1,3,4,6-Tetrahydroxy-helianthrone (30 mg) obtained in Example 3 was dissolved in 10 ml acetone, treated with 1 g potassium carbonate, 0.6 ml dimethyl sulphate and refluxed for 24 hours. The reaction mixture was then stirred for 30 minutes with 20 ml water and then extracted with 50 ml ethyl acetate. The organic extract was dried with magnesium sulphate, filtered and evaporated in vacuum to dryness, to give 28 mg of 1,3,4,6-tetramethoxy-helianthrone.
UV-vis (EtOH) λ$_{max}$ 458, 348, 331 nm NMR δ (CDCl$_3$)3.96 (6H s 3,4-OCH$_3$) 4.15 (3H s 1-CH$_3$) 4.24 (3H s 6-CH$_3$) 6.91 (2H s 2,5-H) 7.25 (2H,t,d J=12.5, 1.5 Hz, 9,14-H) 7.45 (2H,t,d J=12, 1.4, 10,13-H) 7.65 (2H,d, J=8 Hz, 7,12 - H) 8.28 (2H, d J=8 Hz, 8,11-H).

Example 5: Preparation of 10,13-dimethyl-1,3,4,6-tetramethoxy-helianthrone (dimethyl-TMH).

The 10,13-dimethyl-1,3,4,6-tetrahydroxy-helianthrone (50 mg) obtained in Example 1 was dissolved in 20 ml acetone, treated with 1 g potassium carbonate, 1 ml dimethyl sulphate and refluxed for 24 hours. The reaction mixture was stirred for 30 minutes with 30 ml water and then extracted with 50 ml ethyl acetate. The organic extract was dried with magnesium sulphate, filtered and evaporated in vacuum to dryness, to give 40 mg of 10,13-dimethyl-1,3,4,6-tetramethoxy-helianthrone.
UV-vis (EtOH) λ$_{max}$ 458,348,331 nm
NMR δ (CDCl$_3$) 2.13 (6 H s 10, 13-CH$_3$) 3.96 (6 H s 3,4-OCH$_3$) 4.13 (3H s 1-CH$_3$) 4.21 (3H s 6-CH$_3$) 6.88(2H s 2,5-H) 7.254 (2H,q J=10 Hz, 3 Hz) 7.55 (2H s 10,13-H) 8.28 (2H,d J=8 Hz).

Example 6: Preparation of 1,6-di(N-butylamino)-3, 4-dimethoxy-helianthrone

The title compound was prepared by amination of 1,3,4, 6-tetramethoxy-helianthrone with butyl amine. Thus, 44 mg of 1,3,4,6-tetramethoxy-helianthrone were dissolved in 4 ml butyl amine. After warming for two hours at 100° C., the solution was left for 48 hours at room temperature. The solution was evaporated to dryness, and the residue was chromatographed on silica gel using as an eluent a mixture of ethyl acetate:hexane 1:1, to give 35 mg of the title compound 1,6-di-N-butylamino-3,4-dimethoxy-helianthrone.

UV-vis (EtOH) $\lambda_{max}$ 652,577,459 nm

H-NMR δ ppm 11.76 (2H t, J=5 Hz, H—NH), 8.55 (2H d, J=7.5 Hz H-8,15), 7.96 (2H d, J=10 Hz H-11,12), 7.50 (2H t, J=5 Hz H-9,14), 7.27 (2H t, J=5 Hz H-10,13), 6.49 (2H s, H-2,5), 4.09 (6H $CH_3O$—Cl, 6), 3.51 (4H N-butyl), 1.91 (6H, N-butyl), 1.62 (4H N-butyl), 1.06 (4H N-butyl), 0.97 (2H N-butyl).

Example 7: Preparation of 1,6-di(N-butylamino)-3,4-dimethoxy-10,13-dimethyl-helianthrone The title compound was prepared by amination of 10,13-dimethyl-1,3,4,6-tetramethoxy-helianthrone. Thus, 26 mg of 10,13-dimethyl-1,3,4,6-tetramethoxy-helianthrone were dissolved in 3 ml butyl amine and warmed for two hours at 85° C. The reaction mixture was dissolved in ethyl acetate, washed with diluted HCl and water and then evaporated to dryness. The residue was chromatographed over silica gel with ethyl acetate:hexane 1:1, to give 20 mg of the title compound 1,6-di-N-butylamine-3,4-dimethoxy-10,13-dimethyl-helianthrone.

UV-vis (EtOH) $\lambda_{max}$ 652,577,459 nm.

H-NMR δ ppm 8.41 (2H d, J=7.5 Hz, 8,15-H), 7.78 (2H s, 11,12-H), 7.27 (2H t, J=4 Hz 10,13-H), 6.45, (2H s, 2.5 H), 4.06 (6H s, 3,4 $OCH_3$), 3.81 (4H, butyl), 3.54 (4H, butyl), 2.14 (6H s, 10.13 $CH_3$), 1.59 (4H, butyl), 1.34 (2H butyl), 0.95 (6H butyl).

Example 8: Preparation of 1,6-di(N-hydroxyethylamino)-3,4-dimethoxy-helianthrone The title compound was prepared by amination of 1,3,4,6-tetramethoxy-helianthrone with ethanolamine. Thus, 0.2 g of 1,3,4,6-tetramethoxy-helianthrone were dissolved in 4 ml pyridine and treated with 3 ml butyl amine. After warming for two hours at 120° C., the solution was left for 48 hours at room temperature, then evaporated to dryness, and the residue chromatographed, using a mixture of ethyl acetate-:hexane 1:1 to give the title compound 1,6-di-N-ethanolamino-5,6-dimethoxy-helianthrone.

UV-vis (EtOH) $\lambda_{max}$ 625,577,4.59

H-NMR δ ppm 11.89 (2H t, J=5 Hz, H—NH), 8.49 (2H d, J=10 Hz H-8,15), 7.96 (2H d, J=10 Hz H-11,12), 7.50 (2H t, J=5 Hz H-9,14), 7.27 (2H t, J=5 Hz H-10,13), 6.49 (2H s, H-2,5), 4.09 (6H $CH_3$O-Cl,6), 3.51 (4H, N-butyl), 1.91 (6H, N-butyl), 1.62 (4H, N-butyl), 1.06 (4H N-butyl), 0.97 (2H, N-butyl).

Example 9: Preparation of 2,5-dibromo-1,3,4,6-tetrahydroxy-helianthrone 1,3,4,6-Tetrahydroxy-helianthrone (40 mg) was dissolved in acetic acid (20 ml), heated at 75° C. while stirring and then treated with 1 ml of a solution containing 0.8 ml of bromine in 25 ml acetic acid. The reaction mixture was kept at 75° C. for three hours and then evaporated to dryness. The dry residue was chromatographed on silica gel. The title compound (35 mg) was then eluted with a methanol:ethyl acetate mixture 1:9.

UV-vis (EtOH) $\lambda_{max}$ 493 nm (ε 27 000)

NMR δ (DMSO): 8.50 (2H,d J=8 Hz, C-8,15), 7.85 (2H, d J=8 Hz,C-11,12), 7.55 (2H dd, J=8.,3Hz,C-9, 14), 7.32 (2H dd, J=8,3Hz, C-10, 13)

Example 10 Preparation of 2,5-dibromo-10,13-dimethyl-1,3,4,6-tetrahydroxy-helianthrone 10,13-Dimethyl-1,3,4,6-tetrahydroxy-helianthrone (100 mg) was dissolved in acetic acid (25 ml), heated at 75° C. while stirring and then treated with 3 ml of a solution containing 0.8 ml of bromine in 25 ml acetic acid. The reaction mixture was kept at 75° C. for three hours and then evaporated to dryness. The dry residue was chromatographed on silica gel. The title compound (45 mg) was then eluted with a methanol:ethyl acetate mixture 1:9.

UV-vis (EtOH) $\lambda_{max}$ 497 nm (ε 25 000)

NMR δ (DMSO): 8.5 (2H d, J=8 Hz, C-8,15), 7.61 (2H,s, C-11,12), 7.45 (2H d, J=7.0,Hz, C-9,14), 2.47 (3H s,C-10,11).

(II) BIOLOGICAL SECTION

Experimental Procedures

A. Cell Lines:

Human HL-60 leukemic cells were grown in RPMI-1640 supplemented with 15% fetal calf serum, 100 mM glutamine and 100 units/ml penicillin-streptomycin. Human erythro-leukemia K-562 cells (derived from a chronic myeloid leukemia patient) were grown in the same medium supplemented with 10% fetal calf serum. These cells and the human U251 glioblastoma, U87MG glioblastoma and LAN5 neuroblastoma cells used in the experiments are available from the ATCC. All cell lines were cultured in a humidified 5% $CO_2$/95% air atmosphere at 37° C.

B. Cell Viability:

Cell viability was monitored by the MTT assay which measures reduction of 3-(4,5-dimethylthiazol-2-yl)-2,5-diphenyl tetrazolium bromide to formasan by mitochondria of viable cells as described in Mossman (1983). The cells are incubated with MTT for four hours at 37° C. and analyzed in an ELISA reader at 560 nm. The optical density of formasan generated by untreated cell cultures (O.D. control) is defined as one MTT unit. The number of MTT units in culture samples undergoing treatments is calculated as the ratio ($O.D._{sample}$- $O.D._{blank}$)/$O.D._{control}$).

C. Photodynamic Stress:

Photodynamic (PD) stress is the level of phototoxicity inflicted upon target cells by photodynamic compounds and exposure to light. Light irradiation was performed from a fluorescent source of two parallel 40 Watts tubes placed at a fixed distance of 16 cm and measured to emit an incidence of 4 mWatt/$cm^2$. Light intensities were quantitated using the IL 1350 Radiometer/Photometer, from International Light Inc., USA.

D. Determination of Percentage of Apoptotic Cells:

Percentage of apoptotic cells was determined by light microscopy on cytospin cell preparations stained with May-Grunwald-Giemsa. 400 cells were counted by two individuals, independently, and the data are given as the average of the counts. Apoptotic cells were recognized by their smaller size and nuclei that were fragmented into condensed chromatin bodies.

E. Flow Cytometry Analysis:

Cells harvested five hours after application of photodynamic stress were rinsed with phosphate buffered saline (PBS) and fixed with 70% aqueous ethanol. The cells were then resuspended in phosphate-citrate buffer (PC buffer) pH 7.8 (192 parts of 0.2M $Na_2PHO_4$ and 8 parts of 0.1M citric acid) at room temperature for 30 minutes and stained with propidium iodide in PC buffer containing 10 μg/ml RNase A.

The cells were then analyzed in a Coulter EPICS XL-MCL flow cytometer with the entire field gated to include the various changes that affected the cells.

F. DNA Fragmentation Assay:

DNA fragmentation in cells undergoing apoptosis was assayed as described previously (Lotem et al, 1995). $2\times10^6$ cells pelleted in Eppendorf tubes were lysed in 0.5 ml lysis buffer containing 10 mM Tris-HCl, pH 7.5, 0.6% SDS, 10 mM EDTA and 15 $\mu$g/ml RNA mixture (Ambion Corp., Austin, Tex.). After incubation at 37° C. for 10 minutes, NaCl was added to 1M and the mixture was kept overnight at 4° C. The preparation was spun at 14,000 g for 30 minutes at 4° C., the supernatant collected, phenol extracted and DNA precipitated overnight at −20° C. by adding 1 ml ethanol. The DNA pellet was air-dried, dissolved in 20 $\mu$l TE buffer (10 mM Tris, 10 mM EDTA, pH 7.5) at 4° C. for 24 hours, electrophoresed for four hours at 2 V/cm in 1.5% agarose gel containing 0.5 $\mu$g/ml ethidium bromide and photographed under U.V. light.

Example 11. Photodynamic Effects of Hypericin (HY) and 10,13-dimethyl-1,3,4,6-tetrahydroxy-helianthrone (DTHe) on HL-60 Cell Viability The phototoxicity of HY and DTHe to HL-60 cells, as a function of the applied photodynamic stress, was compared following exposure to two doses of light irradiation: 4.8 or 14.4 Joule/cm$^2$, obtained by irradiation for 20 or 60 minutes, respectively. Cells were plated in duplicate $10^5$ cells/well in 100 $\mu$l of medium in 96 well microplates. HY and DTHe were added at 2X concentrations to yield 200 $\mu$l in final concentrations that range from 0.66–20 $\mu$M with 0.5 $\log_{10}$ dose increments. Irradiation was carried out from a fluorescent source at an intensity of 4 mWatts/cm$^2$ for 0.20 (4.8 Joule/cm$^2$) and 60 minutes (14.4 Joule/cm$^2$). Cell viability was monitored after 16 hours by the MTT assay. The results, shown in FIG. 1, indicate that DTHe exhibited a more potent phototoxic activity in comparison with HY. Cell death with DTHe occurred with an LD$_{50}$ of 1 $\mu$M at 4.8 Joule/cm$^2$, which is about three-fold lower than that of HY (3 $\mu$M). A more potent phototoxic activity of DTHe was also seen at the higher light dose of 14.4 Joule/cm$^2$ (LD$_{50}$ of 0.15 $\mu$M and 0.7 $\mu$M for DTHe and HY, respectively). In DTHe- and in HY-treated cells, cell viability, thus, declined in a dose-dependent) manner of both light incidence and concentration of the compounds (FIGS. 1A and 1B). There was no loss of cell viability when the treatments with DTHe or HY were conducted in the absence of light for the same time length, or when the cells were exposed to light in the absence of the compounds. The results, therefore, indicate that cell death resulted from photodynamic effects.

Example 12: Cell Death Induced by Photodynamic Effects of HY and DTHe

The modes of cell death induced by the photodynamic effects of HY and DTHe were evaluated by comparative microscopy of photosensitized HL-60 cytospin cell preparations. Cells were exposed to HY or to DTHe at concentrations that ranged from 0.65–20 $\mu$M (0.5 $\log_{10}$ increments) and light irradiation at 7.2 Joule/cm$^2$ and cultured for 5 hours. Cytospin preparations were then prepared from 50% of the cells and stained with May-Grunwald-Giemsa. 500 cells were then counted in each preparation. The remaining 50% of the cells were washed with PBS, fixed with 70% EtOH, stained with propidium iodide and analyzed by flow cytometry. Normal, apoptotic and necrotic cells were scored, and the quantitative results are shown in FIG. 2. At the lower dose range of 0.2–2.0 $\mu$M DTHe, the prevalent mode of cell death was apoptosis (FIG. 2A). At 0.65 $\mu$M DTHe apoptosis was the only form of cell death recognizable. However, as doses of DTHe were increased to 6.5–20.00 $\mu$M, cell death occurred via a peculiar form of apparent necrosis. Photoinduced "necrosis" was associated with enlargement of the nuclei and formation of a characteristic perinucleolar, ring-like condensations of chromatin that were resistant to further increases in photodynamic damage (data not shown). With hypericin (HY), formation of apoptotic bodies occurred at $\leq 2$ $\mu$M, but at doses $\geq 2$ $\mu$M cell death was apparently mainly necrotic (FIG. 2B). These findings indicate that, although HY was a less potent photoinducer of cell death, HY-induced necrosis occurred at concentrations that were 3-fold lower than DTHe doses that caused apparent necrosis.

Example 13: Morphology of HL-60 Cell Ceath Caused by Photodynamic Stress Induced by HY or DTHe To further characterize the nature of the degraded DNA in DTHe-treated HL-60 cells, the pattern of DNA digestion by electrophoresis in agarose gels was examined. The patterns were correlated with the morphology of the cells as visualized from cytospin stained preparations assayed for percentage of apoptotic and necrotic cells. The results, suggest that PD stress induced by DTHe and HY caused cell death via an apoptotic mechanism. The apparent necrotic morphology obtained at high PD stress levels resulted from impairment of some elements in the cellular machinery that fragments the cells into discrete apoptotic bodies. The endonuclease appeared to be more resistant to the photo-oxidative damage than the nuclear disintegration process.

Example 14 Effects of Photodynamic Stress Induced by HY or DTHe on K-562 Cells

Photodynamic stress was also applied to K-562 cells with DTHe and with HY and its effect on cell death was analyzed microscopically. K-562 cells were exposed to DTHe (FIG. 3A) and to HY (FIG. 3B) with light (6.4 Joule/cm$^2$) and were cultured for six hours. Cytospin preparations were then prepared, stained with May-Grunwald Giemsa and counted for normal viable cells, apoptotic bodies and necrotic cells. The results, shown in FIG. 3 indicate that, although the sensitivity of K-562 cells to DTHe or HY-mediated photo-toxicity was similar to that of HL-60 cells, K-562 cells appeared less prone to undergo complete photodynamic-induced apoptosis with apoptotic body morphology than HL-60 cells. With HY as the photoactivator almost no apoptotic figures were detected at any of the doses applied and apparently necrotic cells were induced at $\geq 2$ $\mu$M. DNA fragmentation to oligonucleosomes in K-562 cells also occurred at the higher doses of $2\geq\mu$M and 7.2 Joule/cm$^2$ light irradiation, and the dose range for cells with apoptotic morphology (0.2–0.65 $\mu$M (FIG. 3A) was narrower than the apoptotic range seen in HL-60 cells (FIG. 2A).

Example 15: 1,3,4,6-Tetrahydroxy-helianthrone (THe) as a Photodynamic Agent

HL-60 cells $4\times10^5$ ml in medium RPMI-1640 supplemented with 15% fetal calf serum, received 1,3,4,6-tetrahydroxy-helianthrone (THe) at a concentration of 0.65 $\mu$M. The cells were light irradiated with 14.4 Joule/cm$^2$ and incubated in a 37° C. incubator. Samples were then collected 0.5 hours, 1, 2, 3, 4 and 5 hours after light irradiation, concentrated on a glass slide by cytospin, stained in May-Grunwald-Giemsa and scored by microscopy for normal, apoptotic and necrotic cells. The results are shown in FIG. 4. Again apoptosis was the predominant mechanism of cell death induction which peaked three hours after light irradiation.

Example 16: Protection of L-cells from TNF-α Induced Apoptosis by DTHe

The effect of DTHe on TNF-α induced apoptosis (programmed cell death) in murine cells was determined: L-cells were placed in 96 well plates at a concentration of $5 \times 10^4$ cells per well in medium RPMI-1640 supplemented with 10%-serum, 10 μml penicillin and 10 μml streptomycin. After 12 hours, DTHe was administered to the cells at doses of 0.5, 2 and 10 μM followed by TNF-α 100 μM and the cells were cultured for an additional 24 hours at 37° C. (5% $CO_2$). An MTT assay was then performed to assess the cell viability (Mossman, 1983). The results are shown in FIG. 5. Data are averages of triplicate wells ±S.D. from one representative experiment of three performed with this cell line.

Example 17: Effect of DTHe on NK-cell Cytotoxic Activity against K-562 Cells Effect of DTHe on human natural killer (NK) cell mediated cytotoxicity was established by determining the cytotoxic activity of NK cells on K-562 target cells labeled with radioactive chromium ($Na_2^{51}CrO_4$). The target cells were then brought into contact with NK cells isolated from human peripheral blood, and their cytotoxic activity against the K-562 targets was established by measuring the amount of radioactive chromium released from the damaged K-562. The experiment was conducted bringing into contact effector NK-cells (E) and K-562 target cells (T at 2 effector target cell ratios E:T=40:1 and E:T=10:1). The results are shown in FIGS. 6A and 6B.

Example 18: Killing of Malignant Tumor Cells in Culture by Dimethyl-TMH and TMH in the Dark Three human malignant cell lines were evaluated to sensitivity to dimethyl-TMH in vitro. Human U251 glioblastoma, U87MG glioblastoma and LAN5 neuroblastoma cells were plated ($2 \times 10^5$ per well) in 96-well flat bottom microculture plates, treated with dimethyl-TMH and hypericin at dose ranges of 0 (control), 0.1–20 μM in complete darkness for a period of 72 hours. The medium was aspirated, the adherent monolayer was washed with phosphate-buffered saline, and cell viability was monitored by the MTT assay.

FIGS. 7, 8 and 9 show the results for the U251 glioblastoma, LAN5 neuroblastoma and U87MG glioblastoma cells, respectively, comparison of the cytotoxic activity with hypericin being shown in FIGS. 7 and 9. Cell viability was lost in all three after exposure to dimethyl-TMH for at least 72 hours, as measured in MTT viability assays. Loss of cell viability following treatment with dimethyl-TMH in the dark of the two glioblastoma cells was more effective than the treatment with hypericin.

The experiment was then repeated with U251 glioblastoma cells treated with dimethyl-TMH or tetramethoxy-helianthrone (TMH) at dose ranges of 0.1–12 μM in complete darkness. Cell viability was monitored by the MTT assay. The results, in FIG. 10, show that both dimethyl-TMH and TMH exhibited comparable cytotoxic activities to U251 cells.

Example 19 Light-Dependent, Photodynamic Effects of Dimethyl-TMH on Normal Primary Human Peripheral Blood Lymphocytes Human peripheral blood lymphocytes (PBL) are non-proliferating cells in the absence of mitogenic stimuli. The effects of different doses of dimethyl-TMH on PBL were examined in the presence or absence of irradiation with polychromatic white light. PBL (post-mitotic) were plated ($2-10^5$ cells/well) in two separate round bottom 96-well plates (in triplicates). Dimethyl-TMH was added to the cultures. One plate was kept in the dark, and the other was exposed to polychromatic white light at a fluence rate of 8 $mW/cm^2$ for 30 min (a total of 14.4 $Joule/cm^2$). Both plates were then cultured at 37° C., 5% $CO_2$ for 72 hours and cell viability was assayed by the MTT assay. The results, in FIG. 11, show that dimethyl-TMH had no effect on PBL viability in the absence of light, however, photosensitization with light caused cell death with an $LD_{50}$ of approximately 0.65 μM dimethyl-TMH, indicating that dimethyl-TMH is a potent photodynamic reagent.

Example 20: Determination of the Cell Cycle Phases in which Dimethyl-TMH Arrests Malignant Tumor Cells Growth and Proliferation in the Dark Cell cycle and DNA content analyses were conducted in U251 human glioblastoma cells after treatment with 5 μg/ml (10 μM) dimethyl-TMH for 24, 48 and 72 hours, and on LAN5 neuroblastoma cells after 48 hours. The cells were then stained with propidium iodide, washed with PBS and analyzed in a fluorescence activated cell sorter (FACS). A computer program arranged the DNA-related fluorescence as follows: the minimal amount of fluorescence is considered to be one whole set of cellular DNA related to the resting $G_1$ phase. A double amount of fluorescence is considered to be $G_2$ phase, in which the whole genome is duplicated following complete DNA synthesis, and the in-between amounts are considered to be the DNA synthetic S-phase, in which the total DNA synthesis is not yet completed.

The results, shown in FIGS. 12 and 13, reveal that administration of 10 μM dimethyl-TMH to U251 human glioblastoma cells produced cell proliferation arrest at mid-S phase (FIG. 12B). The proportion of cells found in the S-phase increased steadily with the duration of exposure to dimethyl-TMH (FIGS. 12A, 12B, 12C). When the dose of dimethyl-TMH was increased from 10 μM to 20 μM (FIGS. 13B and 13C), an exclusive arrest at the S phase occurred. Fluorescence in situ hybridization (FISH) studies confirmed this imbalance in DNA replication at the gene level. This cell cycle arrest causes the toxic effects which elicits cell death.

Example 21: Anti-tumoral Effect of Dimethyl-TMH in vivo in Squamous Cell Carcinoma-Bearing Mice The effective cytocidal activity of dimethyl-TMH in vitro encouraged the evaluation of its safety and anti-tumoral efficacy profile in tumor-bearing mice. Experiments were carried out in mice bearing tumors derived from the SQ2 highly metastatic anaplastic squamous cell carcinoma (SCC) line. This tumor develops as multifocal centers that spread at the vicinity of the primary tumor and metastases develop approximately two months after cell inoculation. Treatments with 300–600 μM dimethyl-TMH/mouse, administered twice or three-times a week were initiated when the tumors reached 5–7 mm in diameter.

Table 1 shows the results of one of the experiments, in which BALB/c mice were inoculated with $5 \times 10^5$ cells of the SQ2 anaplastic squamous cell carcinoma line, intradermally in shaved backs, 8 mice per group. When the primary tumors reached a diameter of 5 mm, therapy with 300 μM dimethyl-TMH/mouse, administered intraperitoneally twice per week, was initiated. Three weeks after the initiation of therapy, the number of tumor foci, which have developed at the primary tumor site, was recorded. The number of foci, which developed 21 days after start of therapy, was considerably reduced by dimethyl-TMH administered at therapeutic doses that were non-toxic to the animals. In addition to preventing the multifocal spread of this tumor, the primary tumors hardened and fell off in 5 of the treated mice, indicating that complete cure of this tumor may be achieved once treatment regimens are optimized.

TABLE 1

The Number of Tumor Foci observed 21 days after the Start of Therapy with Dimethyl-TMH

| Mice | 1 focus | 2 foci | 3 foci | 4 foci |
| --- | --- | --- | --- | --- |
| Control | 3 | 0 | 2 | 5 |
| Dimethyl.-TMH | 8 | 1 | 0 | 0 |

Example 22: Survival of Squamous Cell Carcinoma-Bearing Mice Treated with Dimethyl-TMH BALB/c mice were inoculated with $5 \times 10^5$ cells of the SQ2 anaplastic squamous cell carcinoma line, intradermally in shaved backs, and then administerd with 12 regimens of 200 $\mu$g/mouse of dimethyl-TMH twice weekly beginning on day 7 after cell inoculation. Animal survival was then followed. The results are shown in FIG. 14.

Example 23: The Utilization of Dimethyl-TMH in Antineoplastic Therapy of Malignant Tumors in Mice The antineoplastic effects of dimethyl-TMH in vivo can be examined in a number of murine experimental tumors. These include Esb murine lymphoma, MCA-105 sarcoma and B16 melanoma which are evaluated in C57BL/6J mice. DA3$^{hi}$ murine breast carcinoma cells, a highly metastatic variant of DA3, which generates metastatic breast adenocarcinoma in BALB/c mice, and A431 cells which generate epidermoid tumors in NIH Swiss mice, are evaluated for sensitivities to treatment with dimethyl-TMH or with TMH. Tumors are propagated in mice, 8–10 animals per group, by intradermal inoculations of tumor generating cells. Dimethyl-TMH dose escalations ranging between 20–1000 $\mu$M (10–500 $\mu$g/mouse) are examined. Frequencies of administrations are varied from daily administrations, 3x weekly to 1x weekly, administered for periods ranging from 2–12 weeks. Animals are monitored for differences in primary tumor size compared to untreated tumor bearing control mice. To analyze for spread of metastases all mice are sacrificed at the death of the first control group mouse or at times designated for termination of the experiment. Endpoints used in previous examples are applied. Spleen, liver and lung weights are parameters which we use for determination of metastatic load. Total number of metastatic foci in each of these organs is a second parameter determined after fixation in Bouins solution. Animal survival is another endpoint that is examined. The mean and median survival times, after tumor cell inoculation, is determined. The significance of prolongation of survival is calculated by comparison to controls of untreated tumor bearing animals without exposure to light (compound's dark effects), in the Paired Student's t-test.

In one experiment, the anti tumoral activity of dimethyl-TMH to human tumors in an in vivo model is currently being evaluated in the C.B-17 SCID mouse strain (Fox Chase). Human epidermoid and glioblastoma tumors have been induced in the skin of these mice by inoculation with the corresponding human cell lines. The animals are then subjected to various dimethyl-TMH treatment protocols, the compound administered intraperitoneally. The animals are monitored for tumor size and for survival

Example 24: The Utilization of Dimethyl-TMH in Photodynamic Therapy of Malignant Tumors in Mice Three experimental systems can be used to generate primary tumors with moderate to high metastatic properties from cell lines to study the effects of photodynamic therapy with dimethyl-TMH (dmTMH-PDT) on primary tumor eradication and on metastases. Breast adenocarcinoma tumors generated with DA3$^{hi}$ cells and a poorly differentiated anaplastic squamous cell carcinoma (SCC), generated with the SQ2 cell line are analyzed in BALB/c mice. Murine melanoma tumors induced with B16.F10, a highly metastatic variant of the melanoma cell line, are examined in C57B1.6 mice.

Mice are inoculated $5 \times 10^5$/mouse intradermally to sites on shaved backs of the animals to facilitate irradiation with light, or into foot pads. When primary tumors develop to <5, 5–10 and >10 millimeters in diameter, dmTMH-PDT treatments are initiated, administering dimethyl-TMH i.p. at doses ranging from 50–400 $\mu$g/20 gram mouse (5–40 mMols/kg). The mice are covered with aluminum foil over a wet towel (to prevent heating) exposing only the tumors to irradiation and illuminated with white light. Illumination is applied between 4–16 hours post dimethyl-TMH administration, at a fluence rate of 15 mW/cm$^2$, measured at the surface of the tumor, with total light doses of 30, 90 and 180 Joule/cm$^2$. The different light doses are achieved by altering the duration or the intensity of illumination. Between 1–4 PDT regimens can be given at intervals 5–7 days apart to determine, in a controlled manner, whether multiple PDT regimens improve the anti-tumoral and anti-metastatic efficacies of dmTMH-PDT.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

REFERENCES

Couldwell et al, "Hypericin: a potential antiglioma therapy", *Neurosurgery* 35:705–710 (1994)

Diwu et al, "Design, synthesis, and investigation of mechanisms of action of novel protein kinase C inhibitors: perylene quinonoid pigments", *Biochem. Pharmacol.* 47:373–385 (1994)

Hadjur et al, "Photosensitization by hypericin: ESR evidence for singlet oxygen and superoxide anion radicals formation in an in vitro model", *J. Photochem. & Photobiol. B. Biol.* 26:67–74 (1994)

Lavie et al, "Studies of the mechanisms of action of the antiretroviral agents hypericin and pseudohypericin", *Proc. Nat. Acad. Sci.(USA)* 86:5963 (1989)

Lavie et al, "The chemical and biological properties of hypericin—A compound with a broad spectrum of biological activities", *Medicinal Res. Rev.* 15:111–119 (1994)

Lavie et al, "Hypericin as an inactivator of infectious viruses in blood products" *Transfusion* 35:392–400 (1995)

Losiewicz et al, "Potent inhibition of CDC2 kinase activity by the flavonoid L86-8275", *Biochem. Biophys. Res. Commun.* 201:589–595 (1994)

Lotem et al, "Regulation of bcl-2, bcl-XL and bax in the control of apoptosis by hematopoietic cytokines and dexamethasone", *Cell Growth and Differ.* 6:647–653 (1995)

Meruelo et al, "Therapeutic agents with dramatic antiretroviral aActivity and little toxicity at effective doses: aromatic polycyclic diones hypericin and pseudohypericin", *Proc. Nat. Acad. Sci. (USA)* 85:5230–5324 (1988)

Mossman T., "Rapid colorimetric assay for cellular growth and survival: application to proliferation and cytotoxicity assays", *J. Immunogen* 21:235 (1983)

Rodewald et al, "Synthesis of Hypericin and Related meso-Naphthodianthrones by Alkaline Dimerization of Hydroxyanthraquinones", *Angew. Chem. Int. Ed. Engl.* 16:46–47 (1977)

Spitzner, D., "Synthesis of Protohypericin from Emodin", *Angew. Chem. Int. Ed.* 16:46 (1977)

Takahashi et al, "Hypericin and pseudohypericin specifically inhibit protein kinase C: possible relation to their antiretroviral activity", *Biochem. Biophys. Res. Commun.* 165:1207 (1989)

Tang et al, "Virucidal activity of hypericin against enveloped and non-enveloped DNA and RNA viruses" *Antiviral Res.* 13:313–326 (1990)

What is claimed is:

1. A method for inhibiting transduction of cell proliferation signals comprising administering to a patient in need thereof an effective amount of a compound of the general formula (I):

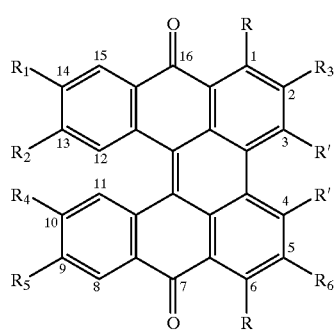

wherein R is selected from the group consisting of hydroxy, $C_1$–$C_{10}$ alkoxy, NH-$C_1$–$C_{10}$ alkyl, and NH-hydroxy($C_1$–$C_{10}$)alkyl; R' is selected from the group consisting of hydroxy and $C_1$–$C_{10}$ alkoxy; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl.

2. The method according to claim 1, wherein treatment is carried out in the absence of light irradiation.

3. The method according to claim 1, wherein treatment is carried out in conjunction with light irradiation.

4. The method according to claim 1, wherein said compound of formula (I) is 10,13-dimethyl-1,3,4,6-tetramethoxyhelianthrone.

5. The method according to claim 1, wherein said compound of formula (I) is selected from the group consisting of:
 1,3,4,6-tetrahydroxyhelianthrone
 1,3,4,6-tetramethoxyhelianthrone
 10,13-dimethyl-1,3,4,6-tetrahydroxyhelianthrone
 10,13-di(methoxycarbonyl)-1,3,4,6-tetramethoxyhelianthrone
 1,6-di-N-butylamino-3,4-dimethoxy-helianthrone
 1,6-di-N-butylamino-3,4-dimethoxy-10,13-dimethyl-helianthrone
 1,6-di-(N-hydroxyethylamino)-3,4-dimethoxy-helianthrone
 2,5-dibromo-1,3,4,6-tetrahydroxyhelianthrone
 2,5-dibromo-10,13-dimethyl-1,3,4,6-tetrahydroxyhelianthrone.

6. A method for treatment of tumors comprising administering to a patient in need thereof an effective amount of a compound of the general formula (I):

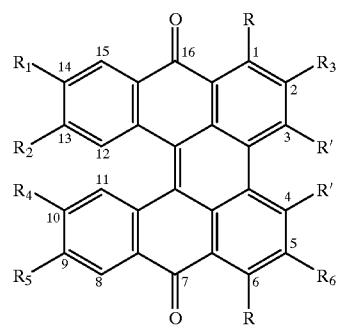

wherein R is selected from the group consisting of hydroxy, $C_1$–$C_{10}$ alkoxy, NH-$C_1$–$C_{10}$ alkyl, and NH-hydroxy($C_1$–$C_{10}$)alkyl; R' is selected from the group consisting of hydroxy and $C_1$–$C_{10}$ alkoxy; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl.

7. The method according to claim 6, wherein treatment is carried out in the absence of light irradiation.

8. The method according to claim 6, wherein treatment is carried out in conjunction with light irradiation.

9. The method according to claim 6, wherein the tumors are malignant.

10. The method according to claim 6, wherein the tumors are metastatic.

11. The method according to claim 6, wherein said compound of formula (I) is 10,13-dimethyl-1,3,4,6-tetramethoxyhelianthrone.

12. The method according to claim 6, wherein said compound of formula (I) is selected from the group consisting of:
 1,3,4,6-tetrahydroxyhelianthrone
 1,3,4,6-tetramethoxyhelianthrone
 10,13-dimethyl-1,3,4,6-tetrahydroxyhelianthrone
 10,13-di(methoxycarbonyl)-1,3,4,6-tetramethoxyhelianthrone 1,6-di-N-butylamino-3,4-dimethoxy-helianthrone
1,6-di-N-butylamino-3,4-dimethoxy-10,13-dimethyl-helianthrone
1,6-di-(N-hydroxyethylamino)-3,4-dimethoxy-helianthrone
2,5-dibromo-1,3,4,6-tetrahydroxyhelianthrone
2,5-dibromo-10,13-dimethyl-1,3,4,6-tetrahydroxyhelianthrone.

13. A method for treatment of solid tumors by photodynamic therapy comprising administering to a patient in need thereof an effective amount of a compound of the general formula (I):

I wherein R is selected from the group consisting of hydroxy, $C_1$–$C_{10}$ alkoxy, NH-$C_1$–$C_{10}$ alkyl, and NH-hydroxy($C_1$–$C_{10}$ )alkyl; R' is selected from the group consisting of hydroxy and $C_1$–$C_{10}$ alkoxy; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl, and irradiating the tumor site with a light source.

14. The method according to claim 13, wherein the tumors are malignant.

15. The method according to claim 13, wherein the tumors are metastatic.

16. The method according to claim 13, wherein said compound of formula (I) is 10,13-dimethyl-1,3,4,6-tetramethoxyhelianthrone.

17. The method according to claim 13, wherein said compound of formula (I) is selected from the group consisting of:
1,3,4,6-tetrahydroxyhelianthrone
1,3,4,6-tetramethoxyhelianthrone
10,13-dimethyl-1,3,4,6-tetrahydroxyhelianthrone
10,13-di(methoxycarbonyl)-1,3,4,6-tetramethoxyhelianthrone
1,6-di-N-butylamino-3,4-dimethoxy-helianthrone
1,6-di-N-butylamino-3,4-dimethoxy-10,13-dimethyl-helianthrone
1,6-di-(N-hydroxyethylamino)-3,4-dimethoxy-helianthrone
2,5-dibromo-1,3,4,6-tetrahydroxyhelianthrone
2,5-dibromo-10,13-dimethyl-1,3,4,6-tetrahydroxyhelianthrone.

18. Compounds of the general formula (I):

I wherein R is selected from the group consisting of hydroxy, $C_1$–$C_{10}$ alkoxy, NH-$C_1$–$C_{10}$ alkyl, and NH-hydroxy($C_1$–$C_{10}$ )alkyl; R' is selected from the group consisting of hydroxy and $C_1$–$C_{10}$ alkoxy; and $R_1$, $R_2$, $R_3$, $R_4$, $R_5$ and $R_6$ are independently selected from the group consisting of hydrogen, hydroxy, chloro, bromo, $C_1$–$C_{10}$ alkyl, $C_1$–$C_{10}$ alkoxy, and $C_1$–$C_{10}$ alkoxycarbonyl, except the compound wherein R and R' are hydroxy and $R_1$ to $R_6$, are hydrogen.

19. The compound according to claim 18, said compound of formula (I) being 10,13-dimethyl-1,3,4,6-tetramethoxyhelianthrone.

20. The compound according to claim 18, said compound of formula (I) being selected from the group consisting of:
1,3,4,6-tetrahydroxyhelianthrone
1,3,4,6-tetramethoxyhelianthrone
10,13-dimethyl-1,3,4,6-tetrahydroxyhelianthrone
10,13-di (methoxycarbonyl)-1,3,4,6-tetramethoxyhelianthrone
1,6-di-N-butylamino-3,4-dimethoxy-helianthrone
1,6-di-N-butylamino-3,4-dimethoxy-10,13-dimethyl-helianthrone
1,6-di-(N-hydroxyethylamino)-3,4-dimethoxy-helianthrone
2,5-dibromo-1,3,4,6-tetrahydroxyhelianthrone
2,5-dibromo-10,13-dimethyl-1,3,4,6-tetrahydroxyhelianthrone.

* * * * *